(12) United States Patent
Fahey et al.

(10) Patent No.: US 11,986,232 B2
(45) Date of Patent: May 21, 2024

(54) SYSTEMS AND METHODS FOR IMPROVED TREATMENT OF HEADACHE

(71) Applicant: Arrinex, Inc., Redwood City, CA (US)

(72) Inventors: Brian Fahey, Menlo Park, CA (US); William Jason Fox, San Mateo, CA (US); Bryant Lin, Menlo Park, CA (US); Vahid Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 517 days.

(21) Appl. No.: 17/259,389

(22) PCT Filed: Jul. 22, 2019

(86) PCT No.: PCT/US2019/042877
§ 371 (c)(1),
(2) Date: Jan. 11, 2021

(87) PCT Pub. No.: WO2020/018999
PCT Pub. Date: Jan. 23, 2020

(65) Prior Publication Data
US 2021/0275241 A1 Sep. 9, 2021

Related U.S. Application Data

(60) Provisional application No. 62/743,471, filed on Oct. 9, 2018, provisional application No. 62/701,379, filed on Jul. 20, 2018.

(51) Int. Cl.
*A61B 18/14* (2006.01)
*A61B 18/02* (2006.01)
(Continued)

(52) U.S. Cl.
CPC .............. *A61B 18/0218* (2013.01); *A61B 2018/00065* (2013.01); *A61B 2018/00238* (2013.01);
(Continued)

(58) Field of Classification Search
CPC ............ A61B 18/02; A61B 18/0218; A61B 2018/00065; A61B 2018/00238;
(Continued)

(56) References Cited

U.S. PATENT DOCUMENTS 6,193,738 B1 * 2/2001 Tomaschko ............ B29C 49/02
606/194
6,491,940 B1 * 12/2002 Levin ................... A61M 11/008
424/434
(Continued)

FOREIGN PATENT DOCUMENTS

WO 2019241697 A1 12/2019
WO 2020006051 A1 1/2020

*Primary Examiner* — Michael F Peffley
*Assistant Examiner* — Amanda L Zink
(74) *Attorney, Agent, or Firm* — McDonnell Boehnen Hulbert & Berghoff LLP

(57) ABSTRACT

The present disclosure provides apparatuses and methods for treating conditions such as chronic daily headache, cluster headache, tension headache, migraine, or acute headache of a patient. In example methods, a cryotherapy element is introduced into the nasal cavity or pterygopalatine fossa to cool or cryoablate at least one of a nasal nerve tissue or nasal blood vessel. The cryotherapy element may be introduced into the nasal cavity in a collapsed position, and prior to cooling a target treatment site may be expanded to an expanded configuration.

12 Claims, 14 Drawing Sheets

(51) Int. Cl.
*A61B 18/18* (2006.01)
*A61B 18/00* (2006.01)

(52) U.S. Cl.
CPC .............. *A61B 2018/00327* (2013.01); *A61B 2018/00345* (2013.01); *A61B 2018/00434* (2013.01); *A61B 2018/00583* (2013.01); *A61B 2018/0212* (2013.01); *A61B 2018/0262* (2013.01)

(58) Field of Classification Search
CPC .......... A61B 2018/00327; A61B 2018/00345; A61B 2018/00434; A61B 2018/00583; A61B 2018/00916; A61B 2018/0212; A61B 2018/0262
See application file for complete search history.

(56) References Cited

U.S. PATENT DOCUMENTS

| | | |
|---|---|---|
| 2015/0031946 A1 | 1/2015 | Saadat |
| 2015/0164571 A1* | 6/2015 | Saadat .................... G01M 3/24 600/109 |
| 2016/0045277 A1 | 2/2016 | Lin |
| 2017/0231474 A1 | 8/2017 | Saadat |
| 2018/0103994 A1 | 4/2018 | Fox |
| 2018/0125560 A1 | 5/2018 | Saadat |
| 2018/0344411 A1 | 12/2018 | Fahey |
| 2019/0290865 A1 | 9/2019 | Fahey |
| 2021/0137610 A1 | 5/2021 | Saadat |

\* cited by examiner

```
┌─────────────────────────────────────────────┐
│  ADVANCING A COOLING INSTRUMENT CONFIGURED TO│
│    DELIVER CRYOTHERAPY INTO THE NOSTRIL OF THE│
│                    PATIENT                   │
└─────────────────────────────────────────────┘
                       │
                       ▼
┌─────────────────────────────────────────────┐
│ POSITIONING THE INSTRUMENT PROXIMATE TO AT LEAST│
│   ONE OF A NERVE OR BLOOD VESSEL WITHOUT     │
│  FRACTURING OR PENETRATING BONE OR CARTILAGE │
│                    TISSUE                    │
└─────────────────────────────────────────────┘
                       │
                       ▼
┌─────────────────────────────────────────────┐
│    APPLYING A CRYOGENIC TREATMENT FROM THE   │
│  INSTRUMENT TO COOL A TARGET TISSUE AND TISSUES│
│  NEARBY THE TARGET AREA TO MODIFY A PROPERTY OF│
│  THE TARGET TISSUE OR TISSUES NEARBY THE TARGET│
│   AREA AND TREAT AT LEAST ONE OF CHRONIC DAILY│
│  HEADACHE, CLUSTER HEADACHE, TENSION HEADACHE,│
│     MIGRAINE, OR ACUTE HEADACHE SYMPTOMS     │
└─────────────────────────────────────────────┘
```

*FIG. 13*

ADVANCING A COOLING INSTRUMENT CONFIGURED TO DELIVER CRYOTHERAPY INTO THE NOSTRIL OF THE PATIENT

↓

POSITIONING THE ACTIVE PORTION OF THE INSTRUMENT AGAINST THE MUCOSAL WALL PROXIMATE TO THE SPHENOPALATINE FORAMEN

↓

APPLYING A CRYOGENIC TREATMENT FROM THE COOLING INSTRUMENT THAT TRAVERSES THE MUCOSAL TISSUE AND UNDERLYING BONE OR CARTILAGE TISSUE AND ALTERS AT LEAST ONE PROPERTY OF THE SPHENOPALATINE GANGLION IN ORDER TO TREAT AT LEAST ONE OF CHRONIC DAILY HEADACHE, CLUSTER HEADACHE, TENSION HEADACHE, MIGRAINE, OR ACUTE HEADACHE SYMPTOMS

*FIG. 14*

SYSTEMS AND METHODS FOR IMPROVED TREATMENT OF HEADACHE

RELATED APPLICATIONS

This application is the US national phase under 35 U.S.C. § 371 of International Application No. PCT/US2019/042,877, filed Jul. 22, 2019, which claims the benefit of priority to (i) U.S. Provisional Application No. 62/701,379 entitled "SYSTEMS AND METHODS FOR IMPROVED TREATMENT OF HEADACHE," filed on Jul. 20, 2018, and (ii) U.S. Provisional Application No. 62/743,471 entitled "SYSTEMS AND METHODS FOR IMPROVED TREATMENT OF HEADACHE," filed on Oct. 9, 2018, the contents of each of which are hereby incorporated by reference in their entirety.

FIELD

The present disclosure is related to the field of treatment of various headache disorders, and is particularly related to thermal treatments, for example cryotherapy cooling or cryoablation.

BACKGROUND

Headache disorders, including migraine, cluster headache, tension headache, and other headache subtypes such as those described generally by the term chronic daily headache, have broad prevalence and are often disabling to those who are afflicted, resulting in substantial patient suffering and significant economic costs due to both treatment expenses and lost productivity. For example, over 28 million people in the United States have suffered a migraine in the past year. Migraine is a primary headache disorder that typically presents with unilateral throbbing pain and may be accompanied by nausea and blurred vision. Migraines may be triggered by a wide variety of internal (e.g., stress, sleep irregularities) or external (e.g., climate changes, alcohol intake) factors. Cluster headache is characterized by severe and recurrent unilateral pain which often is felt around the eye. Headaches typically last up to three hours and may occur daily or multiple times daily for extended periods of time. This pattern often repeats annually or biannually. Chronic daily headache is not a specific diagnosis but describes a condition where headaches occur at least 15 days per month for at least 3 months. Chronic daily headaches may include a variety of headache subtypes (for example, migraine, cluster headache, tension headache, new daily persistent headache) and often manifest bilaterally. Short-lasting, unilateral, neuralgiform headache attacks with conjunctival injection and tearing (SUNCT) syndrome and other headache disorders are more rare, but can be equally excruciating.

The mainstay of treatment for most headache disorders are abortive medications that are available both over the counter (such as acetaminophen, non-steroid anti-inflammatories, and combination agents with caffeine) and by prescription (triptans, ergotamines, butalbital, and narcotics). These agents are intended to provide acute relief of the symptoms of an active headache. Other agents may be used for prophylactic treatment in an attempt to prevent headaches. However, these medications have limited effectiveness in many patients, and may be accompanied by undesirable side effects. For these reasons and others, alternative treatment approaches are desirable.

A number of acute and chronic headache disorders have nervous system origins, for example origins related to sensory and/or autonomic dysfunction. Trigeminal Autonomic Cephalalgia (TAC) is a classification of primary headache types that are related to nervous system function. The trigeminal nerve has been a focus for potential interventions, with particular focus on limiting the activation of the trigeminal parasympathetic reflex, as increased parasympathetic tone may trigger a cascade of events leading to headache onset.

The trigeminal parasympathetic reflex is involved in many headache disorders, including cluster headache and migraine, and describes a positive feedback phenomenon involving both sensory and autonomic nerves. The triggers to the onset of the feedback loop may vary, and spasm or dilation of cerebral blood vessels may mechanically activate nociceptors proximate to the cerebrovasculature and/or dura. Activation of these sensory afferent fibers in the ophthalmic branch (V1) of the trigeminal nerve causes local release of neuropeptides such as calcitonin gene-related peptide (CGRP) which may exacerbate vessel dilation. Signals from the activated nerve endings travel to the trigeminal ganglion and regions known as the trigeminocervical complex that are proximate to the brain stem. Neural activity in this region may result in activation of the superior salivatory nucleus of the facial nerve, thus initiating a reflex arc where sensory activation of trigeminal afferents may subsequently activate parasympathetic efferents. The efferent parasympathetic flow from the facial nerve involves the greater (or superficial) petrosal nerve, which joins with sympathetic fibers from the deep petrosal nerve to form the vidian nerve. Parasympathetic fibers from the vidian nerve synapse in the sphenopalatine ganglion (SPG—also referred to as the pterygopalatine ganglion), and post-ganglionic fibers from the SPG travel to the brain and innervate the cerebrovasculature. With activation of the trigeminal parasympathetic reflex, parasympathetic tone increases and activated parasympathetic fibers may release nitric oxide, vasoactive intestinal peptide (VIP), acetylcholine, and/or other vasodilators near major cerebral vessels, exacerbating dilation and/or spasm even further.

Given the numerous anatomical structures involved in the trigeminal parasympathetic reflex, there are a number of possible treatment sites for an intervention to interrupt this feedback loop, which may provide relief and/or allow prevention of headache symptoms. Directly treating the trigeminal ganglion or nerve root has been attempted, but access is challenging and may be accompanied by risk. Since the parasympathetic efferent component of the trigeminal parasympathetic reflex is mediated via nerves that synapse in the SPG, the SPG, surrounding nerves, and nasal vasculature have been identified as potential targets for intervention to address headaches.

The SPG is the largest and most superior ganglion of the parasympathetic nervous system. It contains sensory, motor, sympathetic, and parasympathetic nerves, although only parasympathetic nerves synapse in the ganglion. It is located in the pterygopalatine fossa (PPF), posterior to the middle nasal turbinate under a relatively small (approximately 1-2 millimeters (mm)) layer of connective and/or mucosal tissue. This triangular or heart shaped structure receives its sensory roots and motor fibers from the maxillary nerve, its parasympathetic root is derived from the nervus intermedius of the facial nerve via the greater petrosal nerve, and its sympathetic fibers derive from the superior cervical ganglion. The PPF can be accessed via the nasal cavity via the sphenopalatine foramen (SPF). The relatively superficial location of the SPG allows simpler access relative to the trigeminal nerve, and the SPG has therefore been a structure of interest for those seeking improved headache treatment options. Various sensory, sympathetic, and parasympathetic nerves, including the posterior nasal nerves (PNN) and the accessory posterior nasal nerves (APNN), travel beyond the ganglion into various regions of the nasal cavity and into other anatomical regions.

Current interventions targeting the SPG to treat headache have associated challenges and/or limitations in terms of effectiveness or practicality. For example, invasive cryo-ablation techniques generally involve the fracture or puncture of bone or cartilage. Other interventions include radiofrequency (RF) ablation, topical or injected application of substances such as lidocaine or bupivacaine, direct or indirect stimulation of one or more nerve bundles, and treatment with neurotoxins such as botulinum toxin. Drawbacks to these approaches may include one or more of the following: limited or inconsistent efficacy, lack of suitability in certain patient populations, the need for invasive implantation of devices or components, the need for repeated procedures, the need for treatment to be repeated over periods of weeks, suitability for only acute relief, and significant pain and morbidity associated with procedures.

Intranasal devices that utilize evaporative cooling may be used in an attempt to address the symptoms of an active headache. However, the current technology available applies intranasal hypothermia broadly to the nasal cavity and has significant disadvantages, including for example the requirement for consistent treatments with each new headache onset, requirement for a large system with limited portability, the need for long (up to 20 min) treatment times, the requirement of oxygen or a pressurized gas source, the lack of a curative or prophylactic treatment potential, the risk of unwanted brain and systemic cooling, and the risk of serious adverse events.

The phenomena known as trigeminal sensitization may also play a role in headache onset, with or without involvement in the trigeminal parasympathetic reflex. Trigeminal sensitization generally refers to a phenomenon whereby the activation thresholds for the sensory fibers of the trigeminal nerve may be lowered, facilitating their excitation. One mechanism for sensitization may be repeated or frequent excitation—i.e., repeated activation of a nerve may lower the threshold required for additional future activations.

With respect to the trigeminal nerve, sensitization may be complex. The trigeminal nerve has three main branches: the ophthalmic nerve (V1), the maxillary nerve (V2), and the mandibular nerve (V3). These branches merge at the trigeminal ganglion. In animal models, it has been established that cell bodies in the ganglion related to one branch of the trigeminal nerve may communicate with cell bodies related to other branches via a communication system that may rely in part on glial cells. As such, excitation of one branch of the trigeminal nerve may result in sensitization at the ganglion level and thereby sensitize nerve endings associated with other branches. For example, symptoms of allergic or non-allergic rhinitis, including nasal cavity irritation, mucosal swelling, and mucosal contact, may activate nerve fibers related to V2, which could in turn lower activation thresholds for headache associated nerves related to V1. This concept may play an important role for headache onset and duration, and may provide treatment options for abortive or prophylactic headache interventions.

As such, improved systems, devices, and methods for applying a therapy in order to treat a headache disorder or the acute symptoms of an active headache may be desirable.

BRIEF SUMMARY

The present disclosure is related to systems, devices, and methods for applying a therapy in order to treat a headache disorder or the acute symptoms of an active headache. More specifically, the present disclosure relates to applying a hypothermic treatment to a target tissue region in order to treat a headache disorder or the acute symptoms of an active headache. This disclosure is particularly useful when treating patients who have failed to respond to first-line treatment options such as pharmaceutical therapeutics. The present disclosure may additionally or alternatively provide sustained relief to patients who are unable or unwilling to undergo invasive procedures requiring advanced surgery or medical implants and patients who respond poorly to abortive interventions.

It is an objective of the present disclosure to provide methods, devices, and systems that advance the treatment of headache disorders with solutions that improve a balance between long-lasting effectiveness and a less invasive procedure. More specifically, it is an objective of the present disclosure to allow for non-invasive or minimally-invasive cryogenic/hypothermic treatment of sensory nerves, autonomic nerves, and/or blood vessels that are involved with the development of symptoms due to various headache disorders. It is an objective to provide a treatment for headache that may remain effective for an extended period of time without the risks associated with the implantation of a device. Accomplishing this objective is valuable because it will improve the standard of care for headache management in a meaningful way, which will benefit patients as well as the healthcare system more broadly.

It is a further objective of the present disclosure to provide methods, devices, and systems that advance the treatment of the symptoms of active headache and provide acute headache relief. More specifically, it is an objective to provide improved methods, devices, and symptoms for safe, precise, and effective hypothermic treatment of headache symptoms. It is an objective to provide patients with treatment options that have improved simplicity and portability that allow for safe and effective relief of headache symptoms.

Accordingly, in one example, the present disclosure provides a method for treating or preventing a chronic daily headache, cluster headache, tension headache, migraine, or acute headache of a patient. The method includes (a) advancing a non-penetrating cryotherapy element into a nasal cavity of a patient with the cryotherapy element in a first collapsed configuration, (b) contacting the cryotherapy element with a surface of a nasal cavity tissue without penetrating the nasal cavity tissue surface, (c) reconfiguring the cryotherapy element from the first collapsed configuration to a second expanded configuration, and (d) cryogenically cooling a target treatment site with the cryotherapy element in order to treat or prevent a chronic daily headache, cluster headache, tension headache, migraine, or acute headache, wherein the target treatment site comprises at least one nasal nerve tissue or nasal blood vessel.

In another example, the present disclosure provides another method for treating or preventing a chronic daily headache, cluster headache, tension headache, migraine, or acute headache of a patient. The method includes (a) advancing a cryotherapy element into a nasal cavity of a patient, (b) advancing at least a portion of the cryotherapy element into a pterygopalatine fossa of the patient, and (c) cryogenically cooling a target treatment site within the pterygopalatine fossa with the cryotherapy element in order to treat or prevent a chronic daily headache, cluster headache, tension headache, migraine, or acute headache, wherein the target treatment site comprises at least one nasal nerve tissue or nasal blood vessel.

In yet another example, the present disclosure provides another method for treating or prevent a chronic daily headache, cluster headache, tension headache, migraine, or acute headache of a patient. The method includes (a) advancing a cryotherapy element into a mouth of a patient, (b) advancing at least a portion of the cryotherapy element into a pterygopalatine fossa of the patient, and (c) cryogenically cooling a target treatment site within the pterygopalatine fossa with the cryotherapy element in order to treat or prevent a chronic daily headache, cluster headache, tension headache, migraine, or acute headache, wherein the target treatment site comprises at least one nasal nerve tissue or nasal blood vessel.

The features, functions, and advantages that have been discussed can be achieved independently in various examples or may be combined in yet other examples further details of which can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 13 illustrates a method of use of a therapeutic instrument, according to an example.

FIG. 14 illustrates another method of use of a therapeutic instrument, according to an example.

DETAILED DESCRIPTION

The disclosure invention is related to systems, devices, and methods for applying a therapy in order to treat a headache disorder or the acute symptoms of an active headache. More specifically, the present disclosure relates to applying a cryogenic or hypothermic treatment to a target tissue region in order to treat a headache disorder or the acute symptoms of an active headache. The devices and methods disclosed herein are particularly useful when treating patients who have failed to respond to first-line treatment options such as pharmaceutical therapeutics and/or who are unable or unwilling to undergo invasive procedures requiring advanced surgery or medical implants and patients who respond poorly to abortive interventions. Accordingly, the present disclosure may assist with treating chronic or acute headache conditions from which millions of people suffer.

In the following description, various examples of the present disclosure will be described. For purposes of explanation, specific configurations and details are set forth in order to provide a thorough understanding of the examples. However, it will also be apparent to those skilled in the art that the present disclosure may be practiced without the specific details. Furthermore, well-known features may be omitted or simplified in order not to obscure the example being described disclosure.

Various aspects of the disclosure described herein may be applied to any of the particular applications set forth below or for any other types of hypothermic treatment systems or methods. The disclosure may be applied as a standalone system or method, or as part of an integrated medical treatment system.

Figure 1A:
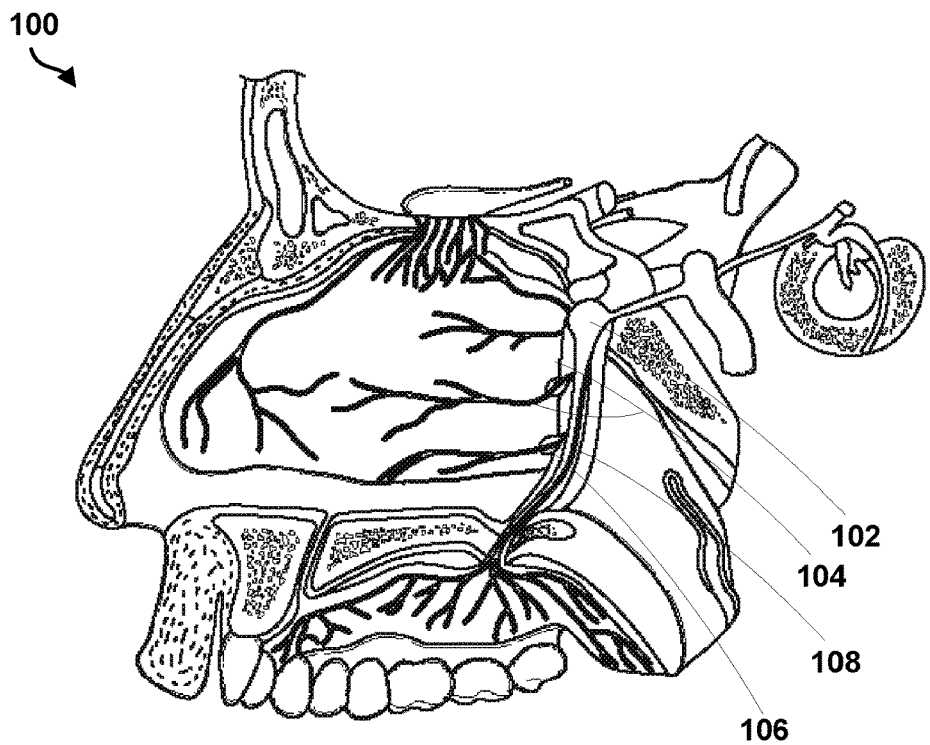
FIG. 1A illustrates the anatomy of nerves in the lateral wall of the nasal cavity and nearby areas.

A selection of the anatomy of the lateral wall of the nasal cavity 100 and surrounding areas with nerves of interest highlighted is illustrated in FIG. 1A. In the illustration, some bony tissues, including the perpendicular plate of the palatine bone, are omitted in order to aid visualization. The SPG 102 is shown posterior to the middle turbinate. The PNN 104 and APNN 106 branch off directly from the SPG 102 or regions nearby, for example in some cases branching off of the greater palatine nerve 108 or nerves proximate to the greater palatine nerve 108. Sensory innervation from the maxillary nerve is also abundant in the nasal cavity 100, though limited views of these fibers are shown in FIG. 1A.

In various examples described herein, headache disorders are treated by applying a hypothermic treatment to tissue regions that include one or more PNN 104 or APNN 106 without specifically targeting regions in the immediate proximity of the SPG 102. For example, treatment placement locations may include locations along the anterior lateral wall, mid lateral wall, and posterior lateral walls, along the inferior turbinate, middle turbinate, or superior turbinates, at the floor of the nose, in the sphenoethmoidal recess, or in the inferior meatus, middle meatus, or superior meatus.

This approach allows for easier access to targeted anatomy and enables outpatient (in-office) procedures that do not require general anesthesia while remaining efficacious at treating headache by selectively interrupting parasympathetic pathways and/or other nervous system pathways that involve the vidian, trigeminal, or other nerves. In examples, cryogen application is configured to cool but not freeze tissue by lowering tissue temperature below normal body temperature. In examples, temperature is lowered by 10-30 degrees Celsius for a period of up to 30 minutes in duration. In examples, treatment times are much shorter, lasting no longer than 5 minutes. In examples, the cryogen application is configured for tissue freezing and cryoablation which may result in tissue damage, necrosis, and apoptosis. In these examples, tissue temperatures may be reduced below 0 degrees Celsius and in some implementations below −15 degrees Celsius. In these examples, the period of cryogen application may be between 10 and 180 seconds.

In examples, headache disorders are treated by applying a hypothermic treatment to tissue regions that include one or more post-synaptic parasympathetic nerve fibers that emerge from the SPG 102. In examples, these tissue regions may include parasympathetic nerve fibers that innervate the cerebrovasculature and/or dura. For example, treatment placement locations may include the sphenoethmoidal recess, regions proximate to the superior turbinate, regions proximate to anterior ethmoid nerve, regions within the maxillary sinus, the choanal arch, regions along the nasal septum, and/or regions along the ethmoid bone proximate to locations of ethmoid foramina. The hypothermic treatments delivered in these regions may be similar to those described above.

In examples, headache disorders are treated by applying a hypothermic treatment to tissue regions that include one or more sensory nerve fibers. In examples, these nerve fibers are branches of the maxillary nerve. For example treatment placement locations may include anterior and posterior locations along the lateral nasal wall and septum, regions along the inferior, middle, or superior turbinates, regions in the inferior, middle, or superior meatus, and tissue regions proximate to the perpendicular plate of the palatine bone. The hypothermic treatments delivered in these regions may be similar to those described above.

Figure 1B:
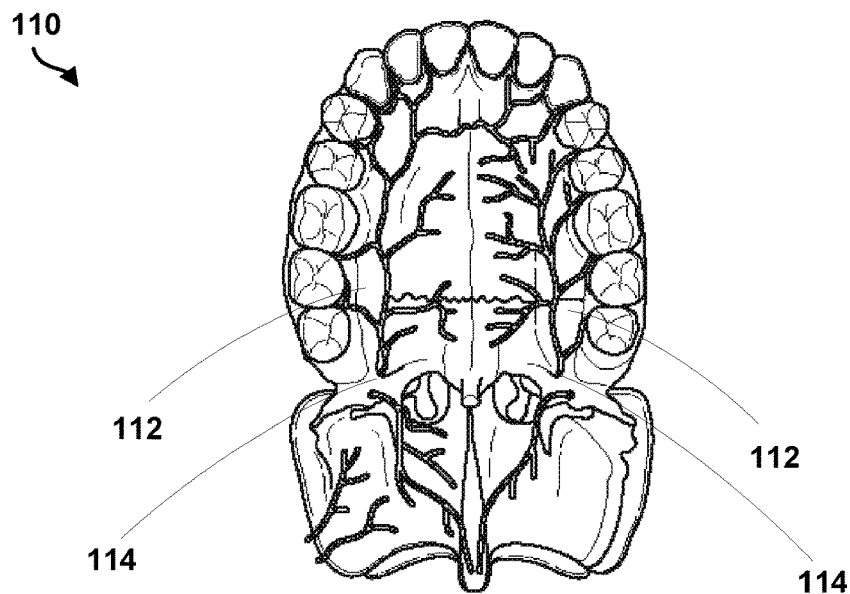
FIG. 1B illustrates an inferior view of the roof of the mouth and selected nerve and blood vessel anatomy.

FIG. 1B illustrates an inferior view of the anatomy of the roof of the mouth 110 with blood vessels and nerves of interest highlighted. As shown, the greater palatine nerve 112 traverses the greater palatine foramen 114 and enters the palatine canal, traveling through the palatine canal to the sphenopalatine fossa where the SPG 102 is located.

Figure 2A:
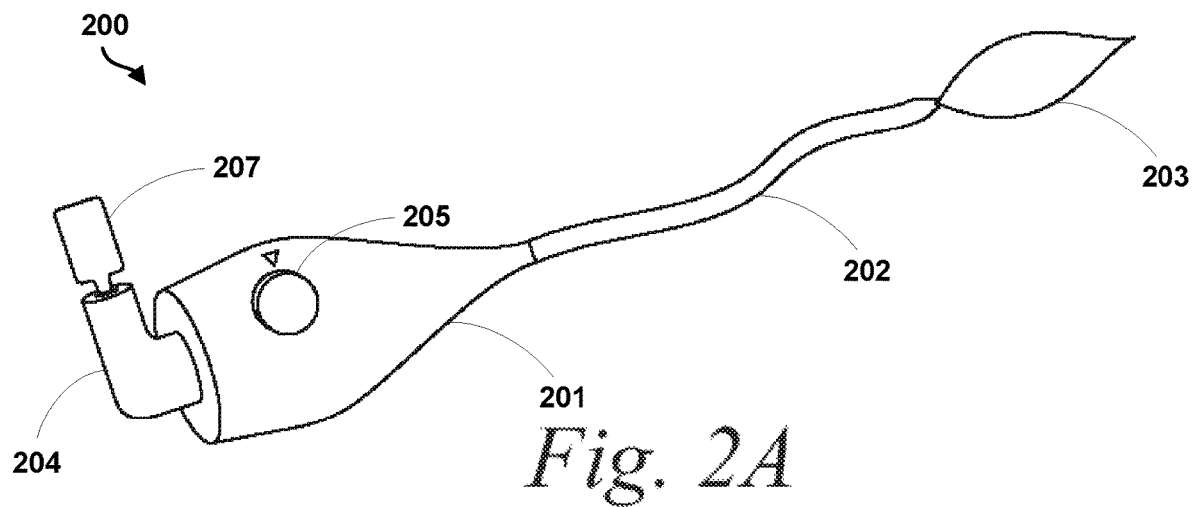
FIG. 2A illustrates a therapeutic instrument, according to an example.

FIG. 2A shows an example of a therapeutic instrument 200 that is adapted to provide hypothermic therapy to tissue regions, for example tissue regions that include the PNN and/or APNN. As shown in FIG. 2A, a therapeutic instrument 200 includes a handpiece 201 and an elongated delivery arm 202. The delivery arm 202 may be malleable and constructed of a material such as aluminum, copper, or annealed stainless steel that allows for an operator to configure the shaft into a desired shape to facilitate insertion into the targeted anatomical location. The distal end of the delivery arm 202 includes a cryotherapy element. For example as shown cryotherapy element is an expandable compliant balloon 203 that is configured to expand from an initially collapsed configuration to an expanded configuration. Balloon expansion occurs distally as well as both superiorly and inferiorly, but primarily in only one lateral direction (i.e. either towards the lateral nasal cavity wall or towards the septal wall). The balloon 203 may be constructed of a thin, soft material, such as rubber, latex or silicone, or other suitable material such as nylon, and given its compliant nature when inflated will interface intimately with adjacent tissues that have a mild to moderately irregular shape. When expanded the balloon 203 may extend between about 0.5 cm and about 3 cm distally from the end of the delivery arm 202 and have a total length between about 1 cm and about 6 cm, and may have a total height between about 1 cm and about 4 cm in the superior-inferior plane. As used herein, the superior-inferior plane is a transverse plane that is parallel to the ground, which (in humans) separates the superior from the inferior or, put another way, the head from the feet. In examples, the distal end of the delivery arm 202 is constructed entirely of soft materials that comprise atraumatic surfaces that are not capable of fracturing or otherwise penetrating tissues.

Figure 2B:
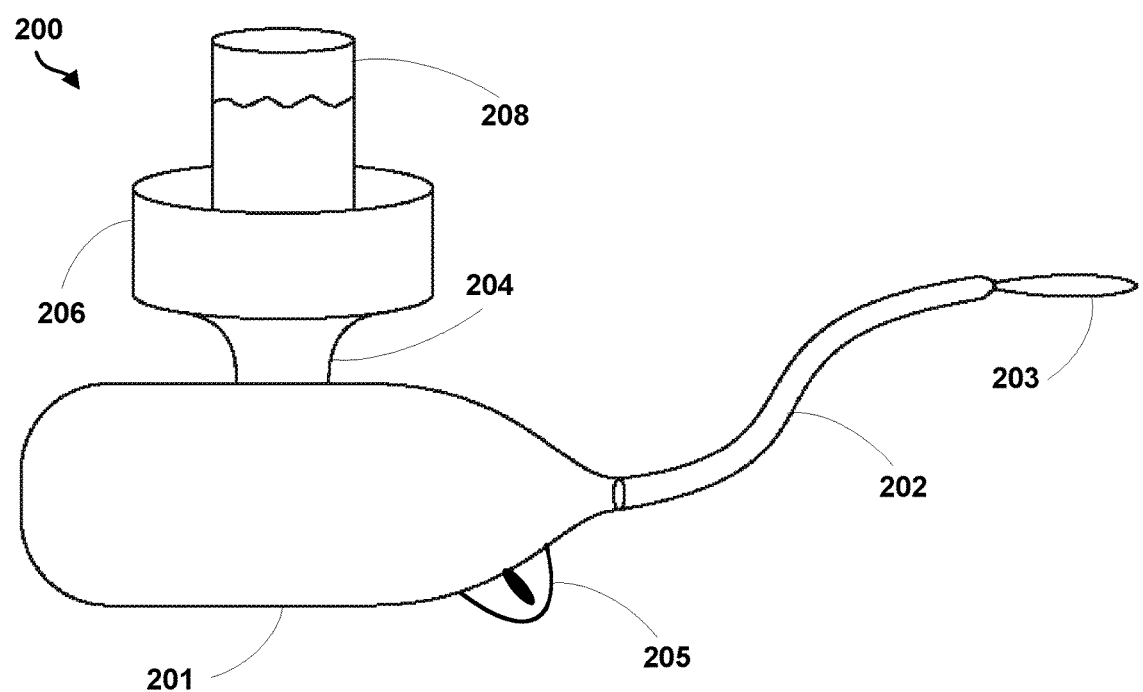
FIG. 2B illustrates another therapeutic instrument, according to an example.

In examples, the handpiece 201 of the therapeutic instrument 200 includes a cryogen intake adapter 204 and a valve interface 205. In examples, the cryogen intake adapter 204 is configured to interface with a cartridge or canister of compressed gas 207, for example a canister of nitrous oxide or carbon dioxide. In examples, for example as shown in FIG. 2B, the cryogen intake adapter 204 is configured to interface with a reservoir of a liquid, for example water, ethanol, or liquid nitrogen. In these examples, the cryogen intake adapter 204 may interface with pumping mechanisms such as those used to circulate fluids in medical systems. In these implementations, a chilling chamber 206 may be located proximate to the cryogen intake adapter 204 in order to reduce the temperature of fluids in a fluid reservoir 208 to a desired temperature. Chilling chamber 206 may use thermoelectric Peltier devices, evaporative cooling techniques, ice baths, phase change materials, or other similar methods to reduce temperatures of liquids stored in reservoirs proximate to the cryogen intake adapter 204.

In examples, the valve interface 205 is a rotatable dial that is rotatable between a first position wherein a valve internal to the therapeutic instrument 200 is in a closed position, to a second position wherein the valve is in an open state allowing a cryogen to flow from the cryogen intake adapter 204 through an internal lumen (not shown) in the delivery arm 202 and reach the distal balloon 203. In examples, a second internal lumen may serve as a return conduit for gases or fluids leaving the balloon. In examples, a second fluid reservoir (not shown) may be included in or near the handpiece 201 to collect fluid that has been circulated through the therapeutic instrument 200. The internal valve may remain in an open position, allowing the flow of cryogen, until an operator rotates valve interface 205 back to the first position, which closes the valve. In examples, valve interface 205 is a push button. The internal valve may be set to be initially in a closed position and remain in a closed position until the valve interface 205 button is depressed by an operator. The valve may remain open while the button is depressed and close when the operator releases the button, or in alternate implementations may remain open after the operator releases the button and close upon the operator depressing the button for a second time.

In examples, the distal balloon 203 is expanded prior to the delivery of cryogen, for example by using a control mechanism on the handpiece 201 to mechanically expand a support structure within the balloon or by delivering a small amount of air or gas into the balloon via a lumen in the delivery arm 202. In examples, the distal balloon 203 remains in a collapsed position until it is expanded by the delivery of a cryogen into the balloon via a lumen in the delivery arm 202.

In examples, the therapeutic instrument 200 is configured such that the distal balloon 203 is porous and as such a cryogen delivered via a lumen in the delivery arm 202 exits the balloon 203 and may be delivered to nearby tissues. In some methods of use, the porous balloon 203 may be adapted to deliver non-cryogenic substances such as anesthetics (including anesthetics utilized as therapeutic agents), antibiotics, saline, or other substances.

Figure 3A:
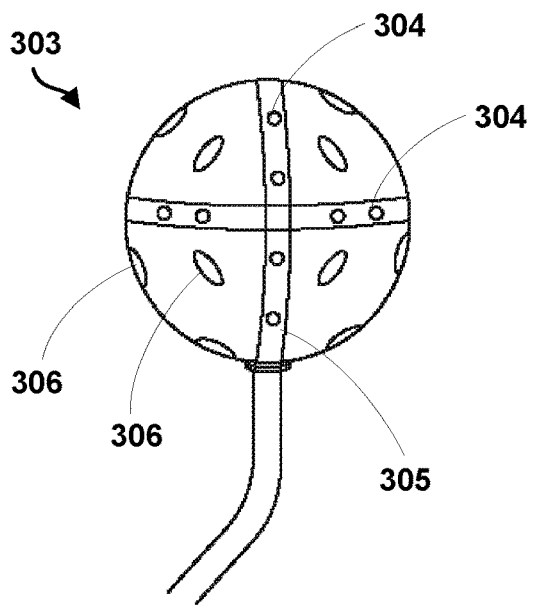
FIG. 3A illustrates a therapeutic instrument that includes distal porous balloons, according to an example.
Figure 3B:
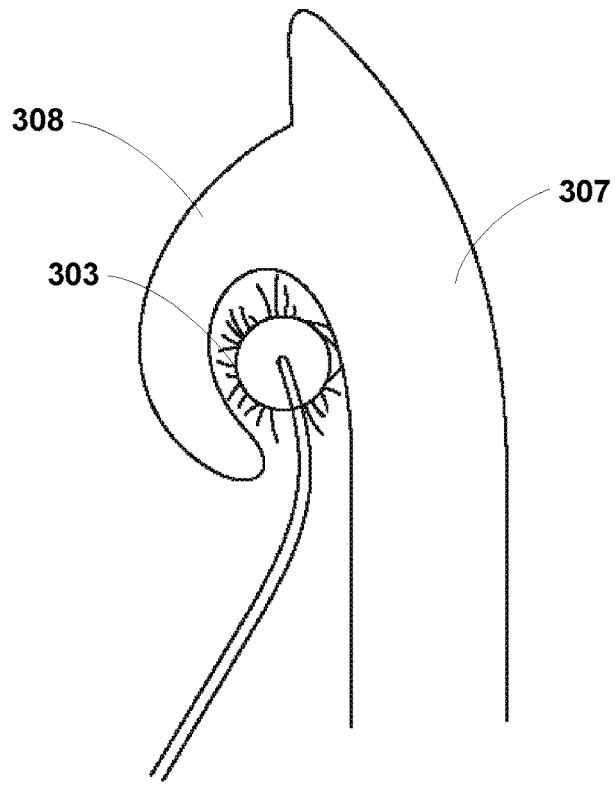
FIG. 3B illustrates a top view of the therapeutic instrument of FIG. 3A, according to an example.

FIG. 3A shows an example in which the cryotherapy element is a porous balloon 303. A cryogen enters the therapeutic instrument via an intake port near the handpiece (not shown) and travels to the porous balloon 303 where it exits via one or more fenestrations 304 in a support structure 305 that is internal to the balloon 303. As an illustrative example, a cryogen transitioning into a gas as it expands produces low temperatures as it exits the fenestrations and is forced out of openings 306 in the balloon 303, thereby cooling nearby tissues. Gas trapped within the balloon 303 also lowers the temperature of tissues at balloon contact points away from openings 306. The presence of openings 306 that allow gas to escape is useful for application to irregularly-shaped anatomies, for example those nearby the lateral wall 307 of the nasal cavity and the middle turbinate 308, where complete balloon contact with target tissues may be difficult to achieve.

In examples, the distal balloon 303 is not porous. As one illustrative example, in examples a delivered cryogen gas is exhausted through fenestrations at the base of the balloon where it meets the delivery arm 202. In examples, a liquid cryogen source is delivered via a closed-loop system where both inflow and outflow lumens are present at the entry point of the balloon, and cryogenic fluids are circulated continuously while a valve is open for active treatment.

Figure 4A:
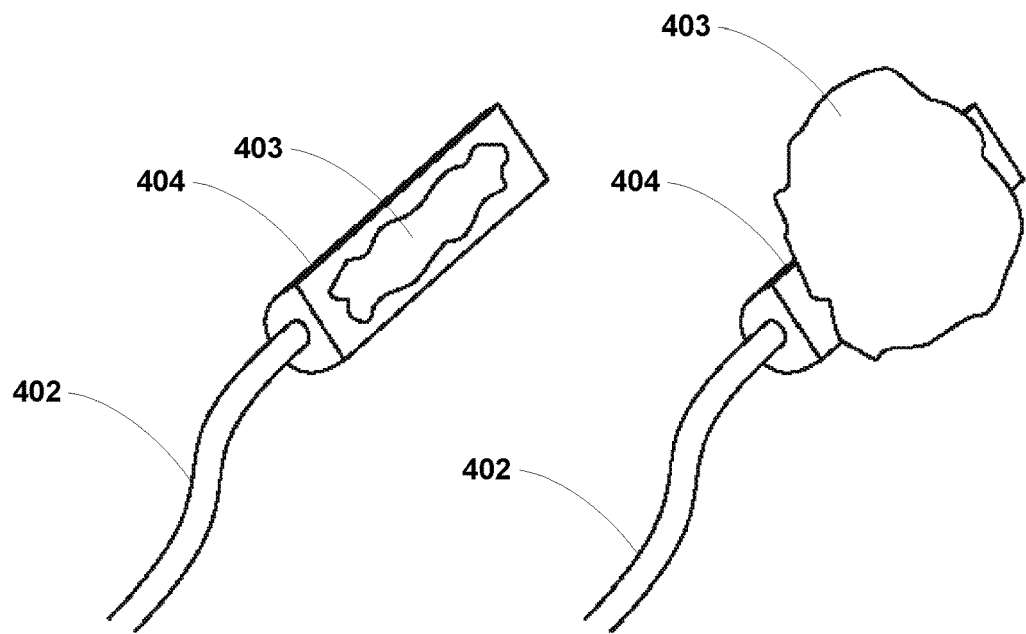
FIG. 4A illustrates a therapeutic instrument that utilizes distal balloons that have both an expanded and an unexpanded state, according to an example.
Figure 4B:
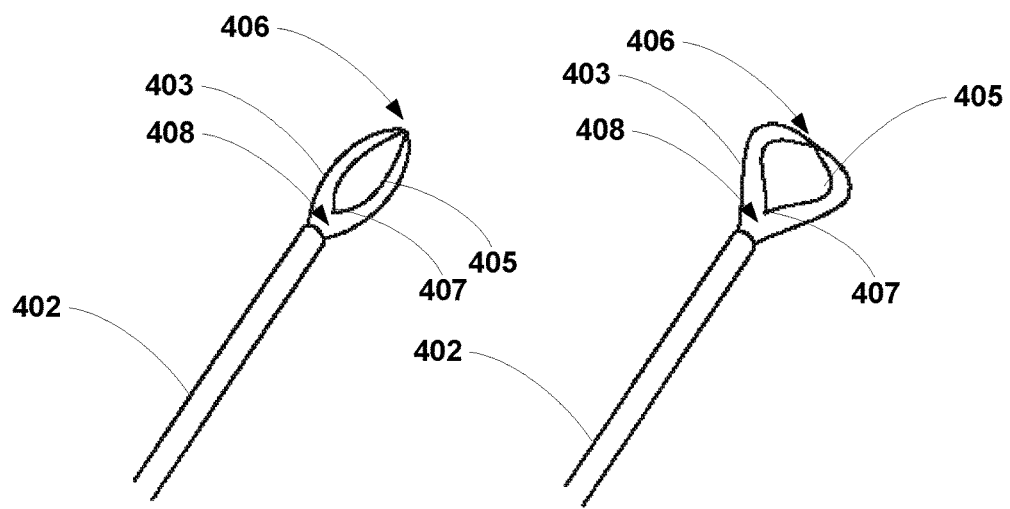
FIG. 4B another therapeutic instrument that utilizes distal balloons that have both an expanded and an unexpanded state, according to an example.

FIGS. 4A-4B show examples of therapeutic instruments in which the cryotherapy element comprises a balloon 403 at the distal end of the delivery arm 402. In FIG. 4A, the flexible and/or malleable delivery arm 402 terminates with a distal applicator 404, in the form of a rigid body. In one particular example, the distal applicator 404 is hemicylindrical in shape and comprised of a rigid material such as steel, brass, or a hard plastic. The distal applicator 404 may range from about 0.5 cm to about 3 cm in length. The medial side of the distal applicator 404 has a smooth curve with polished edges that allow for an atraumatic surface that will minimize the likelihood of injuries resulting from incidental tissue contact. The lateral side of distal applicator 404 is flat and serves as an attachment point for the balloon 403, allowing the balloon 403 to expand primarily in a lateral direction and in the superior/inferior plane (i.e., not in a medial direction toward the solid side of the rigid distal applicator).

In examples, for example as shown in FIG. 4B, devices may include a flexible staging 405 encapsulated by a balloon 403. The staging 405 may be comprised of a thin metal or wire material, for example a wire comprised of Nitinol, that may undergo a shape change or expansion/contraction in response to an operator manipulating a dial, button, or similar control on the handpiece of the apparatus (not shown). This staging material shape change may serve to change the shape of the balloon 403 prior to or following inflation. As one illustrative example, the staging 405 may include a fixed point 406 and a translating connection 407 that moves in accordance with changes in the position of a translating segment 408, which can be adjusted using a dial on the handpiece. As the translating connection 407 moves closer to fixed point 406, flexible staging 405 is bent from a collapsed or oval shape into more of a circular shape, which changes the shape of the balloon 403 that encapsulates the staging 405. The internal staging 405 may be steerable and help manipulate the positioning of the balloon 403, or be utilized to apply pressure from the balloon surface onto an anatomical region of interest. The staging 405 may contain openings or fenestrations that allow for the release of a cryogen gas, or be used as structural support for tubes or lumens involves in a fluid exchange process.

Figure 5:
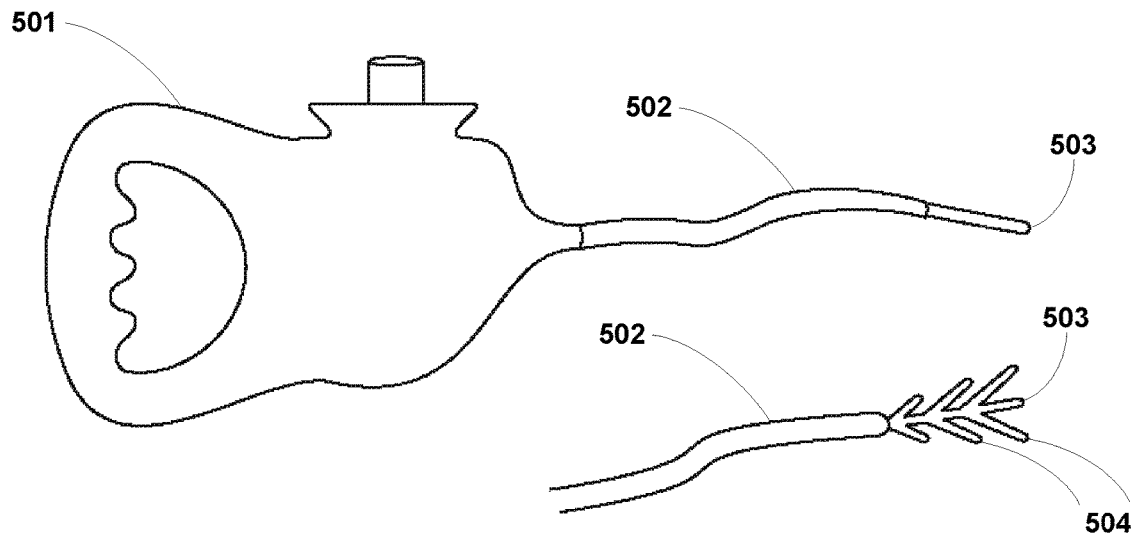
FIG. 5 illustrates an example of a therapeutic instrument that includes a distal tip with expandable tines, according to an example.

In examples, the cryotherapy element at the distal end of the delivery arm terminates in a non-balloon tissue interface, for example as shown in FIG. 5. As show in FIG. 5, the delivery arm 502 extends from a handpiece 501 and terminates in a rigid metallic tip 503. The rigid metallic tip 503 may range from about 0.5 cm to about 3 cm in length, and may be comprised of a rigid, thermally conductive material such as stainless steel or similar materials. The internal portion (not shown) of the metallic tip 503 is adapted to interface with a gas evaporation chamber or fluid circulation heat exchange system, such that cold temperatures are produced internally and transmitted to the exterior portion of the tip via thermal conduction. The metallic tip 503 may be placed in direct contact with target tissues to deliver a hypothermic treatment. As such, the cryotherapy element in this example comprises the rigid metallic tip 503.

In examples, metallic tip 503 includes expandable tines 504 which may fan outward from the body of the tip 503, from a collapsed state to an expanded state. The tines 504 may be constructed of a similar rigid, thermally-conductive material as the main portion of the tip 503. In examples, tip 503 is inserted into the nasal cavity and positioned into place with the tines 504 in a collapsed state and the distal portion of the therapeutic instrument maintaining a slim profile. For example, the tip 503 is positioned proximate to at least one of a mucosal tissue region, a tissue region containing a nerve, or a tissue region containing a blood vessel. In examples, the handpiece may include a control feature such as a dial or button allowing an operator to cause the tines 504 to transition between an expanded state and a collapsed state. The expansion of the tines 504 allows for a greater surface area of tissue to be contacted by a cryogenic treatment device applying hypothermia. In examples, the tines 504 expand primarily in a superior-inferior plane that is parallel to the plane of the tissues in the target tissue region. In examples, the tines 504 may also be capable of movement along one or more additional axes, for example an operator may manipulate a control feature on the handpiece 501 and cause the tines 504 to flex laterally towards tissues in order to establish improved contact or to increase the contact pressure.

In examples, the therapeutic instrument sprays a liquid or gas-based cryogen directly onto target tissues. In examples, fine pores on the distal tip allow for the conversion of a liquid into a fine mist that increases the density of tissue coverage and reduces run-off from target tissues.

In examples, the therapeutic instrument is adapted to penetrate mucosal tissue and deliver hypothermic therapy submucosally. In examples, the distal tip includes a beveled end that allows for the penetration of mucosal tissue and if desired tunneling along tissue planes with or without dissection of tissue away from the wall of a bony region. When in the desired position submucosally, cryogenic treatments may commence that induce tissue hypothermia. The submucosal therapeutic instrument may implement any of the previously described cryogen deployment mechanisms or other cryogen mechanisms.

In examples, the therapeutic instrument is designed to be a completely independent system requiring no additional equipment or adapters for utilization. Any mechanical or electrical components required for operation are contained within the instrument itself, for example contained within the handpiece.

In examples, a therapeutic instrument deploys a thermal insert into the nasal cavity of a subject. The instrument may be inserted into the nasal cavity, deposit an insert into one or more targeted regions, and be withdrawn. In examples, the thermal insert is prepared so as to provide non-ablative degrees of temperature change in order to provide abortive relief of active headache symptoms. In examples, the thermal insert is prepared so as to provide thermal (hot or cold) ablation of tissues in the vicinity of the placement regions in order to provide prophylactic treatment for chronic headache disorders. In examples, the thermal insert may, melt, evaporate, be acutely absorbed, be "blown out" after a period of time, be bioabsorbable over an extended period of time, or be otherwise not retrieved using the therapeutic instrument or another instrument configured explicitly for retrieval. In examples, the thermal insert is adapted to be retrievable by the therapeutic instrument or a separate retrieval instrument.

In examples, the thermal insert is adapted to provide cooling energy to targeted tissues. The thermal insert may be comprised of ice, dry ice, a pre-cooled gel or foam insert, or another suitable material. In examples the thermal insert may be comprised of a phase-change material that maintains a low temperature for an extended period of time while its molecular structure reconfigures during a warming process. The phase change material may have a number of possible phase change transition temperatures, for example 20° C., 0° C., or −20° C. In examples, a cryogen or a phase change material is embedded within a thermally-conductive structure that is placed as a thermal insert. In examples, liquid nitrogen is encased in a structure. In examples, a known volume of a gas such as argon, nitrous oxide, or carbon dioxide is compressed inside of a thermal insert (as part of this compression, the cryogen may change states and become a liquid). The insert may be pierced with one or more puncture holes at the time of placement, and the reduced pressure of the gas within the insert as gas exits via the puncture holes into a larger volume environment will cool the thermal insert and tissues in contact with the thermal insert. The size of the cooling zone, temperature of the thermal insert, and length of the cooling period may be controlled via the design of the thermal insert, for example by controlling the volume of gas included in the insert, the number and size of any puncture holes, and the amount of any insulating materials in the thermal insert.

Figure 6:
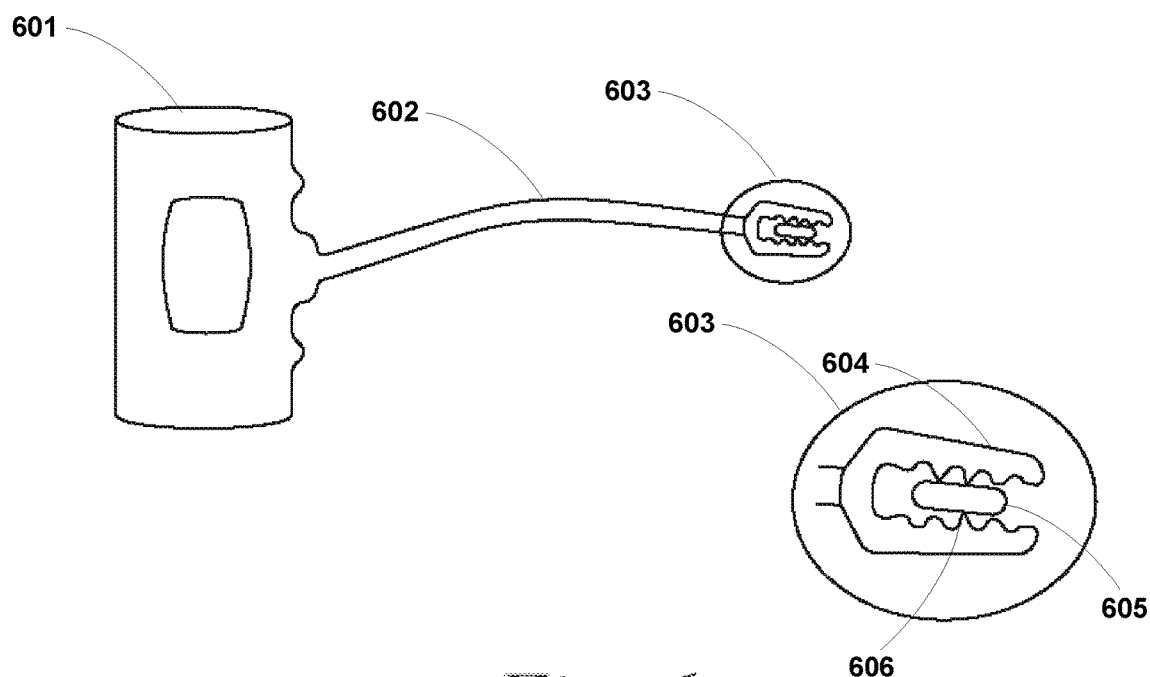
FIG. 6 illustrates an example of cooling/delivery instrument that is adapted to place a thermal insert at a target location, according to an example.

In examples, as shown in FIG. 6, a therapeutic instrument may be configured to deliver a thermal insert. As shown, an instrument includes a proximal end 601 and a distal end 603, which are connected via a steerable shaft 602. Distal end 603 includes a thermal insert delivery member, for example a clasp-like jaw 604, that allows for the instrument to grasp a thermal insert 605. The jaw 604 may include one or more sharp edges 606 that can be utilized to puncture a gas-containing thermal insert 605 upon placement. Controls on proximal end 601 allow for an operator to adjust the position of jaw 604, for example to tighten the jaw to puncture an insert 605 or to release the jaw in order to deposit the insert 605 into a region of interest. In examples, thermal insert 605 may contain a mild adhesive to help secure it in a desired tissue region. In examples where the insert 605 does not contain a compressed gas, the distal end 603 of the instrument may contain a jaw 604 without any sharp edges in order to reduce the possibility of accidental tissue injury. In examples, distal end 603 may include a nozzle structure instead of a jaw, said nozzle configured to spray a cryogenic liquid, mist, foam, or gas into a region of interest. In examples, instruments may also contain an image guidance sensor such as an ultrasound transducer or camera mounted on the shaft 602 proximal to the distal end 603. As such, the cryotherapy element in this example comprises the jaw 604. Data captured by the guidance sensor may be transmitted via wires internal to the steerable shaft 602 and processed using electronics internal to the proximal end 601, and displayed on either a small LCD display screen proximate to the proximal end or transmitted via Bluetooth or similar wired or wireless protocols to a viewing screen external to the main instrument body.

Figure 7A:
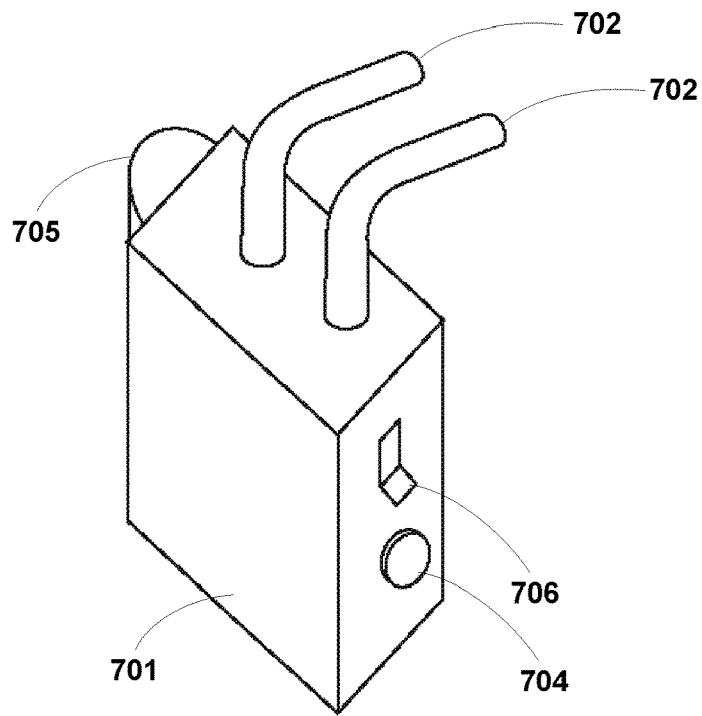
FIG. 7A illustrates a perspective view of a hand-held therapeutic instrument that uses conduits to enter the nasal cavity, according to an example.

In examples, as shown in FIG. 7A, an apparatus may include a hand-held console 701 containing two soft conduits 702 extending from the top side that are angled toward the back side of the console with a small radius of curvature. The conduits 702 are comprised of a thin, soft material, such as rubber, latex or silicone, or other suitable material such as nylon. The conduits 702 may be constructed to be soft and flexible but with enough rigidity to maintain their shape and patency when significant external forces are not applied. The total length of each conduit 702 may be between about 2 inches and about 4 inches. In such an example, the cryotherapy element comprises the conduits 702.

Figure 7B:
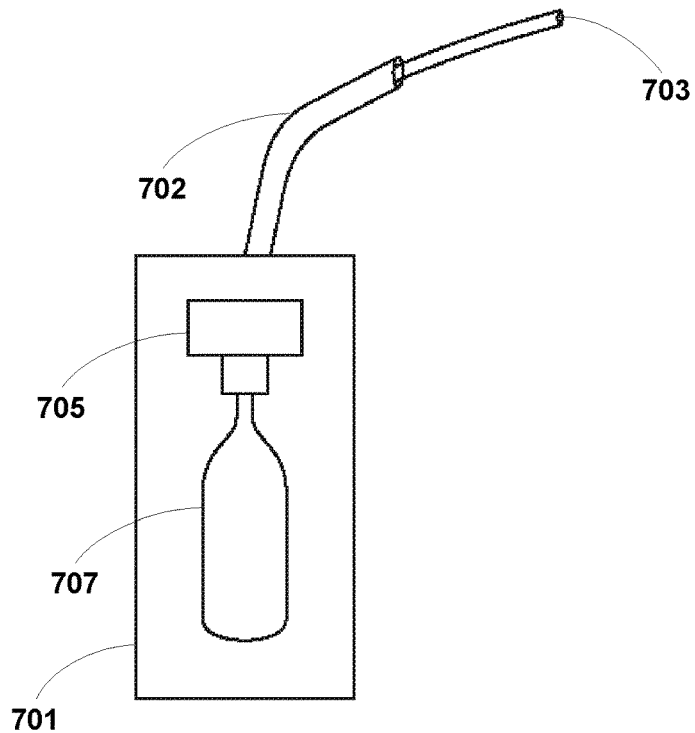
FIG. 7B illustrates a side view of another hand-held therapeutic instrument that uses conduits to enter the nasal cavity, according to an example.

FIG. 7B shows the apparatus in a second configuration, with soft extendable delivery tubes 703 that have been deployed to extend out of the conduits 702. The extendable delivery tubes 703 may be actuated to in response to an action by a user, for example manipulating a dial, knob, button, or other control feature 704 located on the console 701. The delivery tubes 703 may be constructed of a similar soft plastic as the conduits 702 and may be in general more soft and flexible, having column strength sufficient for extension into the nasal cavity but being sufficiently pliable so as to prevent the unintended puncture of any tissue structures they come into incidental contact with. The console 701 may also include an input port 705 for a canister of compressed gas 707 and a second control feature 706 that controls a valve that when placed in an open position allows a cryogen to be deployed outward from the console through the delivery tubes 703. The interior of the console (not shown) may contain various basic electronics (for example, electronics and firmware to power a user interface and the mechanism to extend or retract the delivery tubes 703) and mechanical features (for example, gas evaporator and lumen features). In such an example, the cryotherapy element comprises the delivery tubes 703.

During use, the examples depicted in FIG. 7B may be placed by a user into their nostrils with the apparatus in the first position with delivery tubes 703 retracted internal to the console 701 and/or the conduits 702 (i.e. the conduits are positioned inside the nostrils). Once position has been established, the user may operate the control feature 704 to extend delivery tubes 703 further into the nasal cavity. Subsequent to the extension of delivery tubes 703, the user may manipulate control feature 706 to open a valve and release a cryogen gas, foam, mist, or liquid into selectively targeted regions of the nasal cavity via the delivery tubes 703. A second manipulation of the second control feature 706 disables the cryogen delivery. In examples, the release of the cryogen terminates automatically after a set period of time, for example 15-30 seconds. Following cryogen release, the user may once again manipulate control feature 704 to retract the delivery tubes 703 and remove the apparatus from the nostrils. Performing this process may be used as a method to treat headaches or headache disorders, for example as an abortive treatment to relieve active headache symptoms.

Figure 7C:
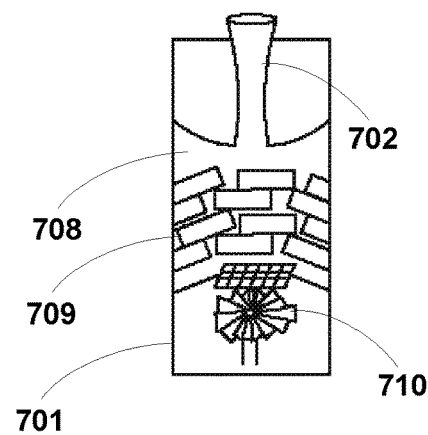
FIG. 7C illustrates a side cross-sectional view of another hand-held therapeutic instrument that uses conduits to enter the nasal cavity, according to an example.

In examples, for example as shown in FIG. 7C, a console 701 may include soft conduits 702 as described above in relation to FIGS. 7A-7B. The console 701 may include rotating fan blades 710 that cause an air flow out of conduits 702. The air flow caused by the fan blades passes through a zone 708 that may warm or cool air prior to it being forced outward through conduits 702 and into a subject's nostrils/nasal cavity. In examples where zone 708 is a warming zone, air is warmed, for example by resistive heating of wires within zone 708, prior to being forced outward through conduits 702. In examples, zone 708 may also condition air, with or without thermal treatments of air, for example by humidifying air or mixing in mists of pharmaceutical or other chemical agents with a nebulizer or evaporation from a wetted sponge. In examples, zone 708 is a chamber that holds a material 709, for example ice, dry ice, a cold phase change material, or another suitable material for cooling the air flow. In examples, heat exchange mechanisms (for example, Freon-based refrigeration systems), Peltier devices, evaporative cooling systems, or other systems are used to cool the walls of zone 708 and the air flow within the zone prior to the air flow passing through the chamber and through the conduits 702 into the nasal cavity.

Figure 8A:
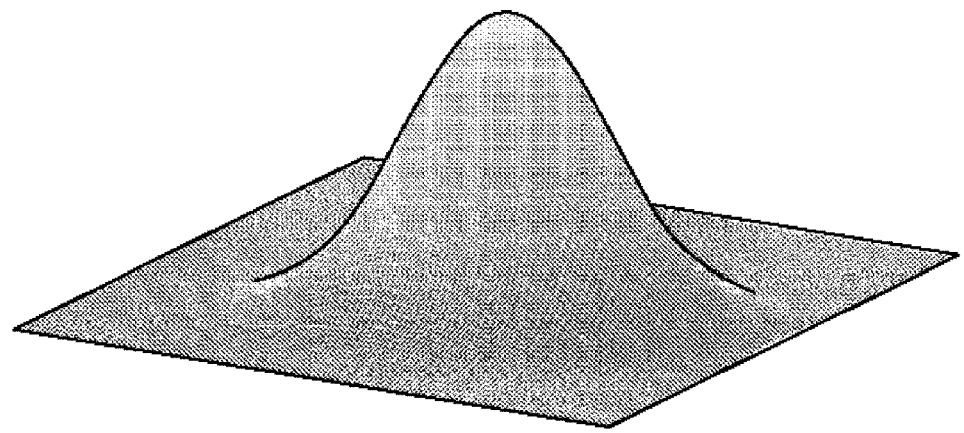
FIG. 8A illustrates a two-dimension normal (Gaussian) distribution.

In examples, devices may include features that help improve the uniformity of a zone of cooling that is applied across a given region. The thermal penetration depth (the depth at which tissues have been reduced to a certain temperature threshold, for example to a least 0° C.) emanating from a spherical source may be shaped similar to a two-dimensional Gaussian distribution, as shown in FIG. 8A. In other words, the depth of cold penetration is expected to be deepest at the location of the cold source (or, with larger cold cryotherapy elements, in the location near the center of the cryotherapy element). For elongated (ex. cylindrical) cryotherapy elements, the shape of the induced cold field will differ but a similar gradual drop-off in penetration depth away from the central portion(s) of the cryotherapy element may be seen. As such, cooling zones may be irregular and a central region of a target treatment area may need to be "over-treated" in order to achieve the desired penetration depth in regions that are distal from the central region, i.e. closer to the edges of the cryotherapy element. Improving the uniformity of the penetration depth of applied temperatures under the cryotherapy element reduces the risk of damage to structures below the treatment zone and may shorten the time required for effective treatment. This is advantageous when treating larger surface areas where the target tissue is thin (for example, mucosal tissues in the upper airway).

Figure 8B:
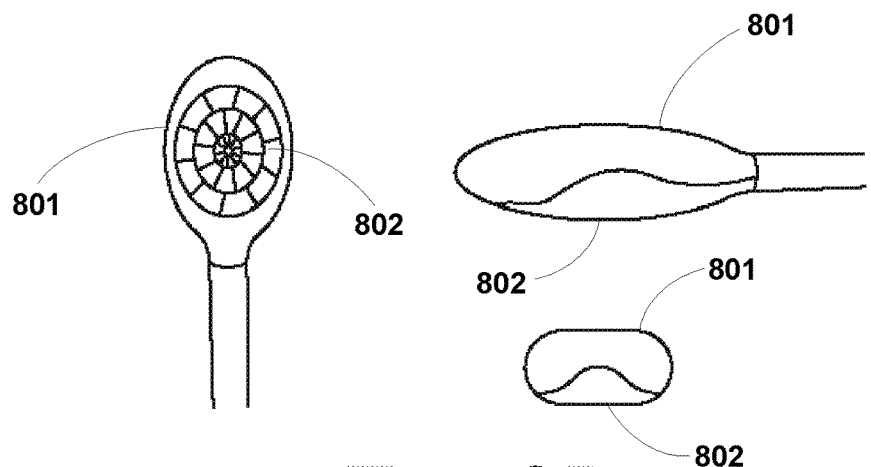
FIG. 8B illustrates an example of a cryogenic balloon with selective insulation, according to an example.
Figure 8C:
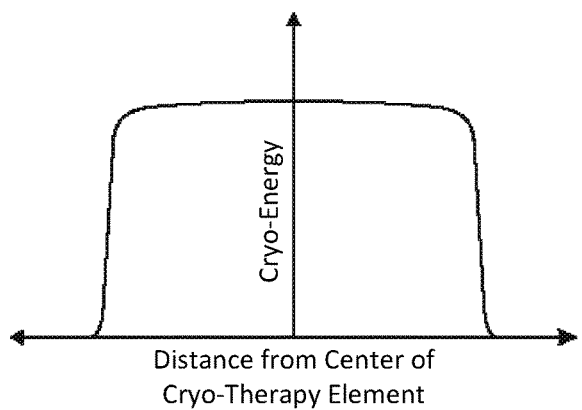
FIG. 8C illustrates an example of a substantially uniform thermal energy distribution.

In examples, for example as shown in FIG. 8B, a cryotherapy element may be configured to produce a substantially uniform cryo-energy distribution. For example, as shown in FIG. 8C, the cryotherapy element may normalize the penetration depth of low temperatures across a larger span of tissues (e.g. "flatten" the Gaussian shaped curves). In examples, a cryotherapy element may be substantially-flat (i.e. less than about 3 mm thick), oval shaped, and include a balloon 801 configured to receive a cryogen liquid or gas delivered to its interior via openings in one or more conduits leading from a cryogen source (conduits not shown for clarity). The balloon 801 may include one or more of various insulating materials, for example gels, foams, air pockets, or viscous fluids. The insulator may have moderate thermal conductivity that provides a mild degree of resistance to thermal conduction from the balloon 801 to adjacent tissues. Hydrogels, other water-based formulations and air pockets are examples of suitable insulation materials. In examples, the insulation materials are distributed to normalize the penetration depth of cold temperatures across a larger span of tissues. For example, as shown in FIG. 8B, an insulator material 802 can be preferentially deposited such that it has the largest thickness in the middle of the balloon 801 and little to no thickness at the edges of the balloon 801, with a gradual transition between these regions. This configuration in provides a mild thermal barrier to the conduction of cold temperatures to tissues proximate to the central portion of the balloon 801 while providing little to no thermal barrier for transfer of thermal energy to tissues proximate to the outer edges of the balloon 801. As such the penetration depth of cold temperatures in the central portion of the treated region of tissue is decreased by the thicker insulation, allowing for a uniform distribution of temperature depth penetration. Examples with uniform distribution of temperature depth penetration may be used to treat symptoms of headache or headache disorders, as well as in the treatment of cancers, rhinitis, sinusitis, and other conditions.

In examples, the thickness of the balloon material is varied over portions of the balloon 801, and no additional insulating material is utilized. In general, the balloon material may be thin (0.013-0.13 mm) to allow for efficient thermal transfer. The balloon 801 may be comprised of a soft rubber or plastic, such as latex, nylon, silicone, polypropylene, polyethylene, or similar natural or synthetic materials. In examples, the balloon material thickness is greatest in the central portion of the balloon 801, and diminishes in thickness gradually towards the balloon exterior.

Figure 9A:
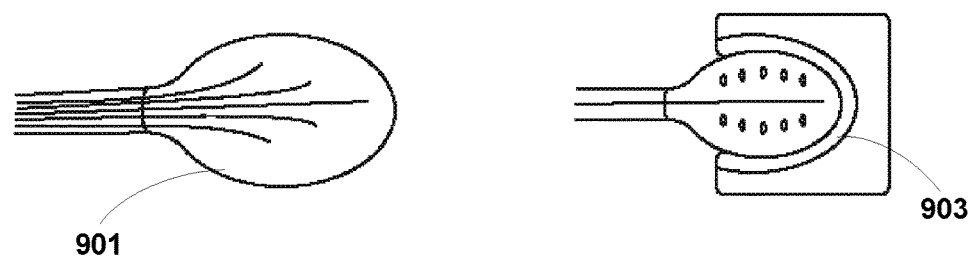
FIG. 9A illustrates a cryogenic delivery device intended to provide hypothermic therapy with a more even depth distribution, according to an example.
Figure 9B:
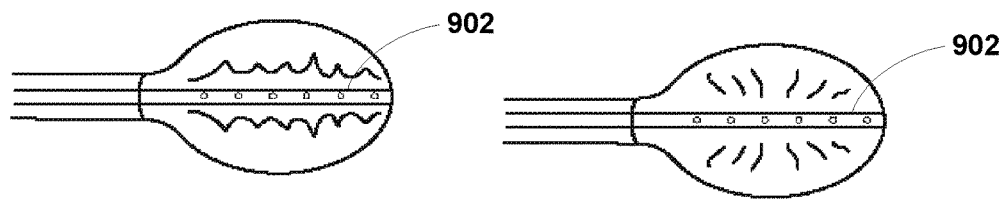
FIG. 9B illustrates another cryogenic delivery device intended to provide hypothermic therapy with a more even depth distribution, according to an example.
Figure 9C:
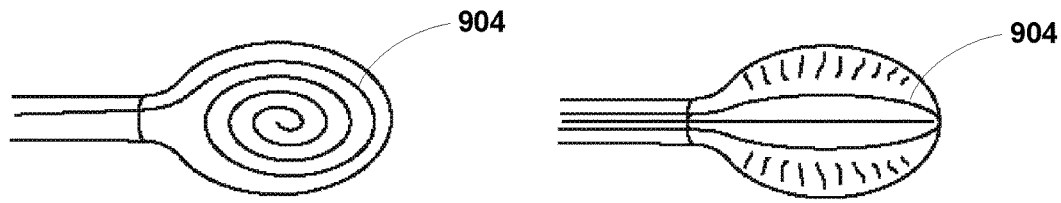
FIG. 9C illustrates another cryogenic delivery device intended to provide hypothermic therapy with a more even depth distribution, according to an example.

In examples, for example as show in FIGS. 9A-9C, a cryotherapy element normalizes the penetration depth of low temperatures across a larger span of tissues. As shown, a cryogen is dispersed evenly throughout the cryotherapy element 901 to minimize the presence of any localized zones with disproportionate cooling. In examples, a compressed cryogen liquid is sprayed through a plurality of nozzles 902 at defined flow rates into the cryotherapy element 901 such that the liquid converts into a gas and uniformly cools the large surface of the cryotherapy element 901 that is in contact with the target tissue 903. In examples, an array of the nozzles 902 is a fixed member(s) within the cryotherapy element 901 (for example, miniature tubes comprised of stainless steel or a polymer). In examples the nozzles 902 may comprise a single tube with an inner diameter less than 0.010 inches and micro pores formed into the side wall of the tube. Micro pores may have a diameter less than about 0.006 inches and may vary in size along the length of the cryotherapy element 901 to improve the uniformity of cryogen dispersion. In examples, a cryotherapy element 901 is comprised of an inner non-compliant flexible cryogen liquid bladder 904 with micro pores created along the outer surface throughout the treatment area of the cryotherapy element 901. The inner cryogen bladder 904 may be affixed and fully enclosed inside the outer tissue contacting non-compliant, semi-compliant, or compliant expandable cooling bladder of the cryotherapy element 901. The inner cryogen bladder 904 will spray liquid cryogen into the outer cooling bladder where the liquid turns into gas and causes the expandable outer cooling bladder to cool uniformly and expand. The outer cooling bladder is able to expand by throttling the exhaust outflow of the cryogen gas from the cooling bladder.

In examples, the effect of hypothermia treatment is enhanced by augmenting the treatment with secondary mechanisms. For example, when targeting blood vessels or tissues nearby blood vessels with hypothermia, the heat sink effect of warm blood flow continuously circulating through a region may limit effectiveness or alter the shape of the affected tissue region in an unwanted or unanticipated manner. Examples may thus temporarily limit blood flow in or proximate to a target tissue region. In examples, other secondary mechanisms may be employed to augment the effects of applying a cryogen to a tissue region. A therapeutic instrument applying hypothermia may be used in conjunction with an ultrasonic or mechanical suction device that may impact the density and/or permeability of tissues and thereby alter the penetration characteristics of the applied thermal field.

Figure 10:
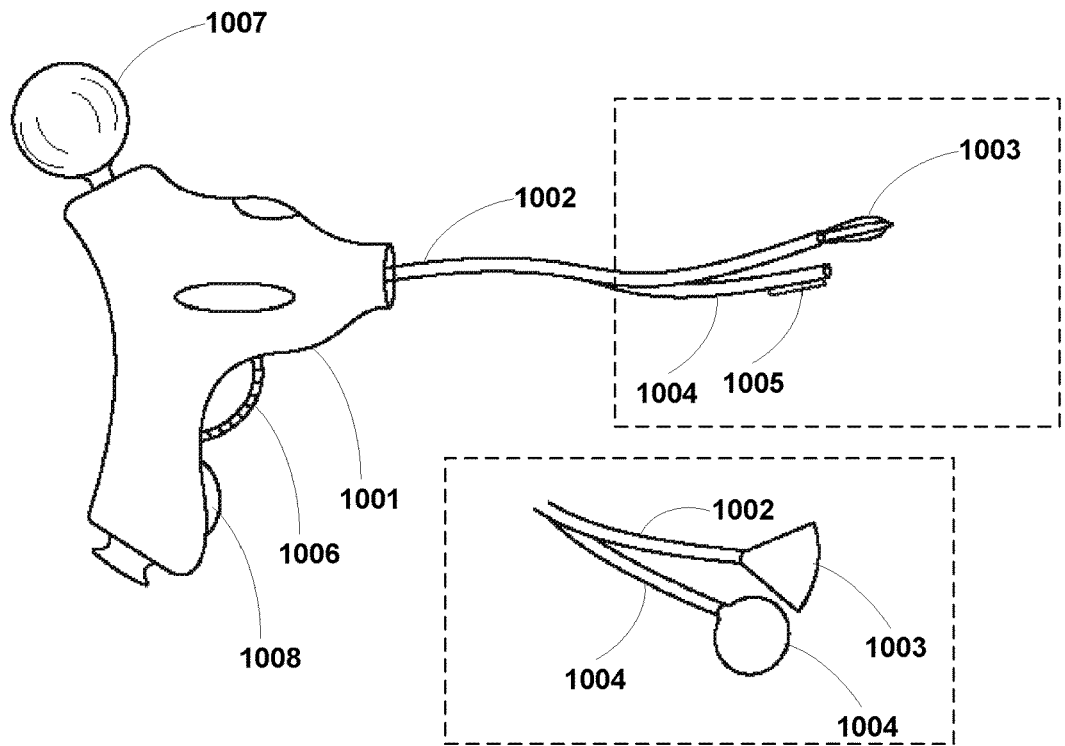
FIG. 10 illustrates a therapeutic instrument that utilizes a balloon to temporarily limit blood flow into a region, according to an example.

In examples, for example as shown in FIG. 10, a secondary mechanism may be used to temporarily reduce blood flow in a region to augment the effect of an applied hypothermic treatment. A therapeutic instrument includes a handpiece 1001, a flexible delivery arm 1002, a cryotherapy element 1003 near the distal end of the delivery arm 1002, and an appendage arm 1004 that terminates in a non-compliant balloon 1005. In a first configuration, balloon 1005 is deflated and appendage arm 1004 is in-line with delivery arm 1002 in order to provide a slim profile instrument which can navigate a narrow and irregularly-shaped space such as the nasal cavity. In a second configuration, the angle of the appendage arm 1004 can be adjusted by a user by manipulating a dial 1006 or another suitable control feature on the handpiece 1001. With or without changing the position of the appendage arm 1004, the balloon 1005 may be inflated by the user by manipulating a second control feature (for example, a button, slider, dial, switch, etc.) on the handpiece 1001. In examples, the balloon 1005 may be inflated by squeezing pumping mechanism 1007 located proximate to the handpiece 1001, which forces air through an internal valve and through a lumen in the delivery arm 1002, causing the balloon 1005 to inflate. Other inflation mechanisms are possible as well.

The balloon 1005 may remain inflated until the balloon pressure is released by opening a valve with a control (not shown) proximate to the handpiece 1001. The inflated balloon 1005 exerts pressure on a tissue region, said pressure being sufficient to reduce or occlude blood flow flowing through nearby vessels. With the tissue heat sink effect limited via reduced blood flow, the user may activate cryogen application by manipulating a third control feature 1008 on the handpiece 1001. One or more of the previously described cryogen delivery mechanisms may then be utilized to deliver a hypothermic treatment to the tissue regions proximate to the cryotherapy element 1003.

In examples, blood flow through one or more vessels is temporarily reduced or occluded using alternative methods, for example mechanical compression methods. In examples, a therapeutic instrument has an expandable distal end with smooth, atraumatic surfaces that a user may deploy to apply pressure in desired tissue regions.

Figure 11:
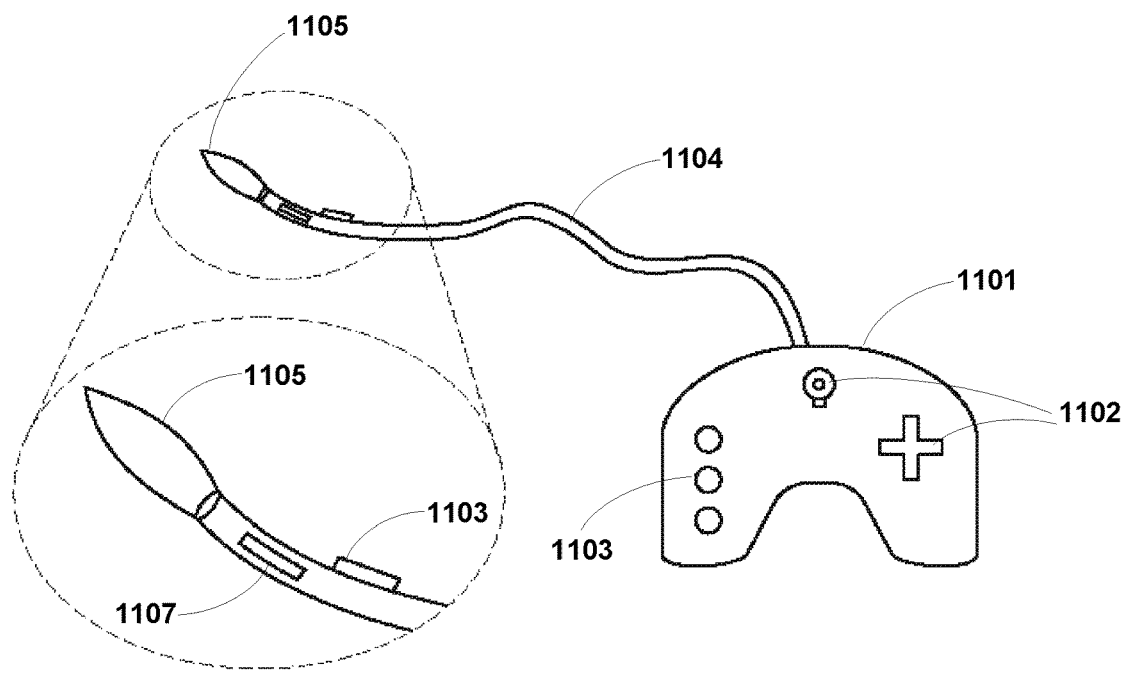
FIG. 11 illustrates a therapeutic instrument with a steerable delivery arm, according to an example.

In examples, for example as shown in FIG. 11, a therapeutic instrument is configured to be inserted into the nasal cavity and access the PPF via the SPF. From within the PPF the therapeutic instrument is configured to provide a hypothermic treatment directly to or in the immediate vicinity of the SPG and/or surrounding blood vessels such as the sphenopalatine artery. The therapeutic instrument is comprised of a proximal controller 1101 configured to have both steering features 1102 and control features 1103. The controller 1101 connects to a flexible delivery arm 1104, the position of which can be at least partially controlled via steering features 1102 on the controller 1101. In examples, the position of the distal tip of the delivery arm 1104 may be manipulated along at least two axes using the controller 1101. In examples, the positions of other segments of the delivery arm 1104, for example the central portion of the arm, may be adjusted using the controller 1101. In examples, movements of the delivery arm 1104 are electronically and/or robotically controlled using motors or mechanical actuators. In examples, the movements of delivery arm 1104 are mechanically controlled with pulleys, wires, gears, or other mechanisms.

The distal portion of the delivery arm 1104 includes a cryotherapy element 1105. In examples, the distal portion of the delivery arm 1104 also includes a visualization feature 1106. In examples, the cryotherapy element 1105 is distal to the visualization feature 1106 such that it is encompassed in the field of view of a visualization feature 1106 configured to examine the distal tip of the delivery arm 1104 and/or the anatomy proximate to the distal tip. In one example, the cryotherapy element 1105 may be a balloon configured to receive a cryogenic gas or liquid, a metallic chamber configured to be cooled via evaporative cooling from a gas, via a circulating fluid, or via an implanted phase-change material, a spray nozzle configured to convey a cryogen outward toward target anatomy, other cryogenic delivery configurations described in this disclosure, or other cryogenic delivery configurations. The internal structure of the delivery arm 1104 as well as some features of controller 1101 may vary in examples depending on the configuration of cryotherapy element 1105. As an illustrative example, in an implementation that utilizes evaporative cooling of a cryogen gas, the proximal controller 1101 may include a canister intake port and delivery arm 1104 may contain lumens to deliver the cryogen from the intake canister to its distal portion which includes the cryotherapy element 1105. The visualization feature 1106 may be a video or photographic camera, an ultrasound transducer, an infrared thermal mapping sensor, an optical coherence tomography probe, or another visualization feature.

In examples, the visualization feature 1106 may be accompanied by a light source 1107 configured to illuminate the field of view, for example light sources similar to those utilized in contemporary endoscopes or fiberscopes. In examples, the visualization feature may provide a two-dimensional image, which may be displayed on a monitor connected to the controller (not shown), on a nearby smartphone or tablet, or on a separate monitor that communicates with the electronics associated with the visualization feature 1106 through wired or wireless connections. In examples, the visualization feature 1106 may provide a binary read-out indicating that the distal portion of the therapeutic instrument is aligned with a target anatomical feature (for example, the SPF). In examples, output from the visualization feature 1106 is transmitted to electronics in the controller 1101 via wires inside or proximate to the delivery arm 1104 and is interpreted using algorithms running in software and/or firmware. If the distal tip of the delivery arm 1104 is determined to be in a suitable location, the operator is informed, for example by electronics and/or software in the controller illuminating an LED, producing an audio tone, producing a mechanical signal such as a vibration of the controller handle, or by using similar notification mechanism.

In examples, the distal tip of delivery arm 1104 enters the PPF by traversing the SPF. In examples, the distal tip of delivery arm 1104 includes a beveled edge that facilitates the penetration of mucosal tissue covering the SPF. In examples, via automated or user-controlled means, the distal tip may be manipulated in a way to dissect local mucosa, adipose, and other soft tissue covering the SPG, allowing for more direct treatment of the SPG. When the distal tip has entered the PPF, a hypothermic treatment may be initiated by delivering a cryogen directly onto structures of interest, by cooling portions of the apparatus that are proximate to structures of interest, by other methods, or by some combination of these methods. In examples, the delivery arm 1104 and distal tip may be adapted to enter the PPF and be positioned to provide cooling proximate to the vidian canal. In examples, the distal tip of the delivery arm 1104 does not enter the SPF directly, but rather aligns and "docks" at the opening into the PPF. In examples, suction delivered via one or more ports (not shown) proximate to the distal tip create a negative pressure vacuum force that helps maintain this position with the distal tip aligned with the opening into the PPF. Negative pressure sources may interface with the controller 1101 and be coupled to the suction ports proximate to the distal tip via airflow lumens inside or proximate to the delivery arm 1104.

In examples, the therapeutic instrument is configured such that it may deploy a gaseous, mist-like, liquid, or solid cryogen directly into the fossa when the distal tip held in place proximate to the SPF. In examples, the therapeutic instrument is configured to deploy an extendable delivery tube (not shown) into the fossa while the thicker delivery arm 1104 remains within the nasal cavity. A cryogen may be delivered or applied to tissues via the delivery arm 1104. This implementation balances the steering capability and maneuverability associated with a semi-rigid delivery arm with the practicality of a less rigid, smaller sized delivery tube that has been designed to enter smaller spaces and provide less risk of mechanical injury to tissues contacted incidentally.

In examples, the therapeutic instrument includes one or more additional features to assist with confirming the location of the distal tip. These additional features may be utilized in lieu of or in addition to a visualization feature to confirm the location of a distal tip. In examples, the additional position confirmation features involves one or more electrodes positioned on the exterior-facing surface of the delivery arm 1104 proximate to the distal tip, as well as associated electronics contained in the interior of the proximal controller 1101. Wires connecting the drive electronics to the one or more electrodes may be included inside the delivery arm 1104 or be attached to the surface of the delivery arm 1104. The electrodes may provide nerve stimulation to nerves which they contact or are nearby, said stimulation initiated by the operator by manipulating at least one control feature 1103 on the controller 1101. The stimulation may be provided in either constant current or constant voltage modes of operation, may be delivered with monopolar, bipolar, or other electrode configurations, and may include the use of symmetric or asymmetric electrical waveforms.

In examples, the intensity of the stimulation may be altered by the operator. For example, the stimulator may be configured to have a limited intensity range between 0-100 mA and 0-50 V (assuming a 500 Ohm load). In examples, motor, sensory, or autonomic nerves, or some combination of these, may be targeted by the nerve stimulator. In examples, the one or more electrodes on the therapeutic instrument may be configured such that the stimulator will induce paresthesias in the subject when the distal tip is located in the correct position.

In examples, a therapeutic instrument is configured to be inserted into the mouth and access the PPF via the greater palatine foramen and the palatine canal. Devices similar to those illustrated in FIG. 11 may be adaptable for this access point with minor modifications, for example a longer active distal tip of the delivery arm or longer delivery tubes to account for the larger distance from the greater palatine foramen to the SPG and nearby vasculature and other possible anatomic targets.

In examples, a therapeutic instrument is configured to be inserted into the maxillary sinus via the nasal cavity or oral cavity and access the PPF via the posterior wall of the maxillary sinus. The posterior wall of the maxillary sinus is comprised of a thin cartilage. Access to the maxillary sinus through the nasal cavity may be accomplished via the posterior fontanelle. Access to the maxillary sinus through the oral cavity may be accomplished via a small incision above the canine. In examples, devices similar to those illustrated in FIG. 11 may be used for this access point with minor modifications, for example a beveled distal end to enable poking through cartilage.

Figure 12A:
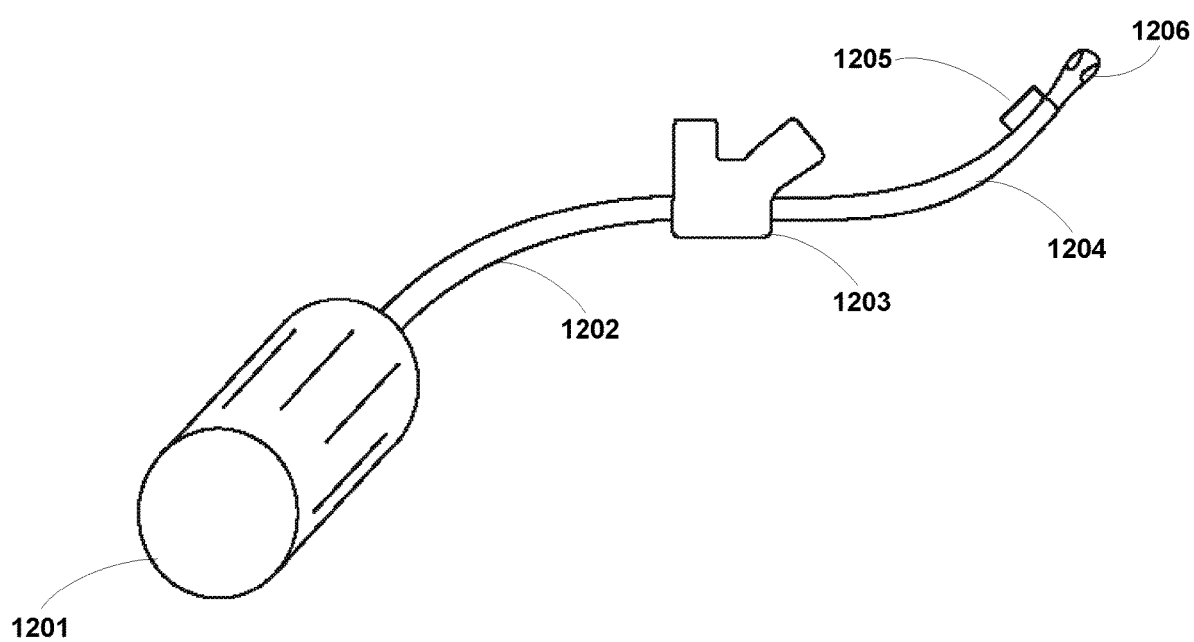
FIG. 12A illustrates a therapeutic instrument with first and second connecting arms as well as the example in use in a subject, according to an example.
Figure 12B:
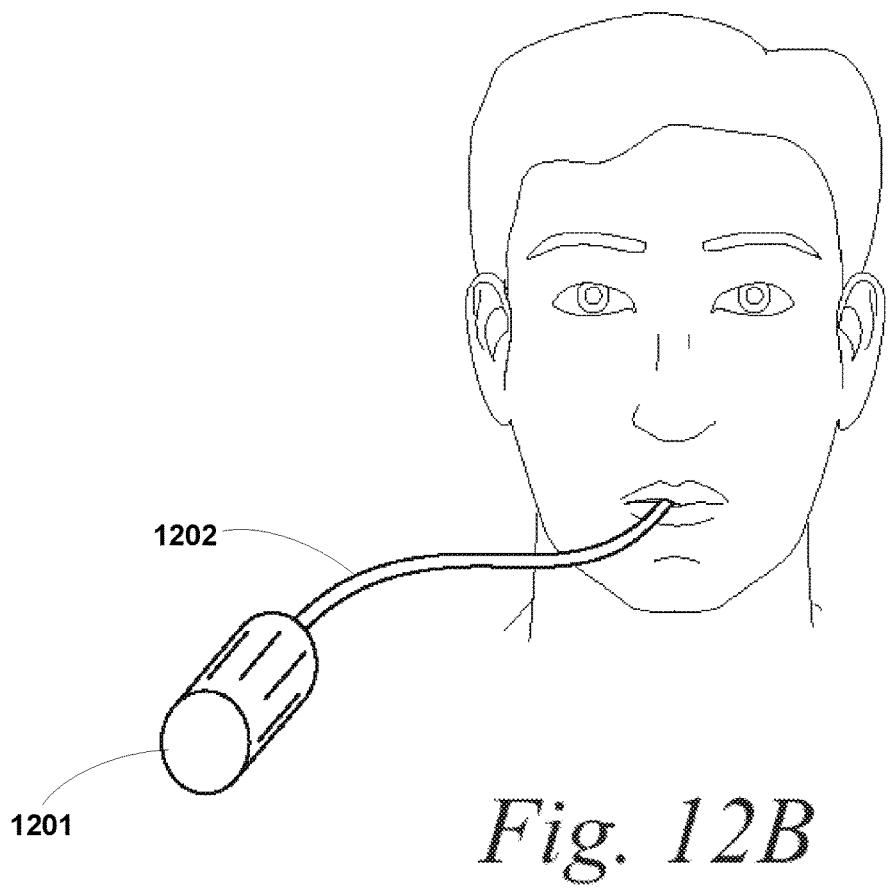
FIG. 12B illustrates the therapeutic instrument of FIG. 12A positioned in mouth of a patient, according to an example.
Figure 12C:
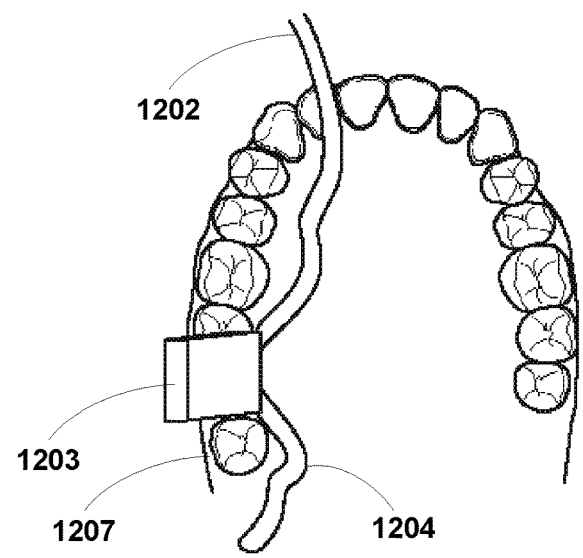
FIG. 12C illustrates the therapeutic instrument of FIG. 12A positioned in mouth of a patient, according to an example.

Examples, for example as shown in FIGS. 12A-12C, may apply hypothermia to the PPF via an access point of the greater palatine foramen. A therapeutic instrument includes a handpiece 1201, a first connecting arm 1202, a locking segment 1203, and a second connecting arm 1204. The handpiece 1201 may include various features including steering and operational controls and at least one input adapter for a cryogen source. For simplicity these features are not shown in FIG. 12. The first connecting arm 1202 is preferably between about 5 cm and about 50 cm in length, and may be comprised of a flexible material such as silicone or another natural or synthetic material. The first connecting arm 1202 includes multiple lumens to serve as conduits for wires/electronics, mechanical components, and/or cryogenic substances. The locking segment 1203 is configured to attach to at least one of the rear molars 1207 inside a subject's mouth, and may be comprised of a more rigid plastic material but have a silicone coating so that it can comfortably sit in a subject's mouth for a period of time. Other material combinations are possible as well.

Such an attachment is illustrated in FIG. 12C, which shows an inferior view of the roof of a subject's mouth. The attachment is accomplished via springs, tongue and groove locking mechanisms, or other releasable-pressure temporary fixation mechanisms. The locking segment 1203 interfaces with both the first connecting arm 1202 and the second connecting arm 1204, and in addition to serving as an anchor mechanism also serves as a conduit to relay at least a portion of the contents contained in the lumens of the first connecting arm 1202 (for example, cryogens and electronics) into the lumens of second connecting arm 1204. In examples, the second connecting arm 1204 is comprised of a semi-rigid material and is of a construction that allows for it to bend into an arbitrary configuration with motion in any axis. The second connecting arm 1204 may be steered using controls located on the handpiece 1201.

Examples may also include visualization components 1205 which may assist an operator in guiding the second connecting arm 1204 into or proximate to the greater palatine foramen 1208. Examples may include one or more electrodes 1206 near the distal tip for applying nerve stimulation as a way to confirm the location of the distal tip, as described previously in this disclosure. In examples, the second connecting arm 1204 is adapted to enter the greater palatine foramen 1208 directly and extend upwards through the palatine canal and into the PPF. In examples, the second connecting arm 1204 is aligned with the greater palatine foramen 1208 and serves as a conduit for a delivery tube (not shown) which is extended out of the connecting arm and into the palatine canal. Once either the second connecting arm 1204 or the delivery tube has been placed, an operator may initiate a hypothermic treatment by activating a cryogen source by manipulating a control on the handpiece 1201. Visualization and other features to confirm the therapeutic instrument is in the proper anatomical location that are described elsewhere in this disclosure may be incorporated in any example. One advantage of examples as shown in FIGS. 12A-12C is that a portion of the therapeutic instrument is anchored in place and therefore limits the time an operator has to spend with their hands inside a subject's mouth. Such an example also limits the amount of time a subject needs to maintain a position with the mouth wide open to provide access to an operator's hands and larger tools, which will improve comfort for the subject.

The devices and systems taught in this disclosure are accompanied by methods of use and methods of treatment of headache disorders, including migraine, chronic daily headache, tension headache, and cluster headache, as well as abortive treatment of headache symptoms. Numerous methods of use/treatment are described herein. In examples, the steps described in the context of one method of use may be included in any of the other methods of use described herein.

Examples of methods of applying a hypothermic treatment to a tissue of a patient in order to treat at least one of chronic daily headache, cluster headache, tension headache, migraine, or acute headache symptoms may include the following steps: (1) advancing a therapeutic instrument configured to deliver cryotherapy into the nostril of the patient; (2) positioning the instrument proximate to at least one of a nerve or blood vessel without fracturing or penetrating bone or cartilage tissue; and (3) applying a cryogenic treatment from the instrument to cool a target tissue and tissues nearby the target area to modify a property of the target tissue or tissues nearby the target area and treat at least one of chronic daily headache, cluster headache, tension headache, migraine, or acute headache symptoms. A diagram of an example of this method is provided in FIG. 13.

In one particular example, of the method disclosed in FIG. 13, the step of advancing a therapeutic instrument configured to deliver cryotherapy into the nostril of the patient may comprise advancing a non-penetrating cryotherapy element into a nasal cavity of a patient with the cryotherapy element in a first collapsed configuration. In such an example, the method may further include contacting the cryotherapy element with a surface of a nasal cavity tissue without penetrating the nasal cavity tissue surface and reconfiguring the cryotherapy element from the first collapsed configuration to a second expanded configuration, prior to applying the cryogenic treatment from the instrument to cool the target tissue.

In examples, in a method, for example as disclosed in FIG. 13, the step of applying the cryogenic treatment may involve applying cooling exclusively within the nasal cavity. In examples of the method disclosed in FIG. 13, the step of applying the cryogenic treatment involves applying cooling exclusively to the lateral nasal wall. In examples of the method disclosed in FIG. 13, the step of applying the cryogenic treatment involves applying cooling exclusively in at least one of the inferior meatus, the middle meatus, or the superior meatus. In examples, for example as disclosed in FIG. 13, a step of applying the cryogenic treatment may involve applying cooling exclusively within the maxillary sinus.

In examples, in a method, for example as disclosed in FIG. 13, the step of applying a cryogenic treatment from the instrument to cool a target tissue may involve cooling a mucosal tissue proximate to at least one posterior nasal nerve or accessory posterior nasal nerve. In examples of the method disclosed in FIG. 13, the step of applying a cryogenic treatment from the instrument to cool a target tissue involves cooling at least one nerve branch originating from the sphenopalatine ganglion. In examples, for example as disclosed in FIG. 13, a step of applying a cryogenic treatment from the instrument to cool a target tissue may involve cooling at least one nerve branch originating from the trigeminal nerve. In examples of the method disclosed in FIG. 13, the step of applying a cryogenic treatment from the instrument to cool a target tissue involves cooling at least one blood vessel proximate to at least one of either the palatine or vidian canal.

In examples, in a method, for example as disclosed in FIG. 13, the step of applying a cryogenic treatment may involve applying cooling exclusively downstream of the sphenopalatine ganglion (i.e. in regions defined by the anatomical locations of nerves that have synapsed or traveled through the ganglion). In examples of the method disclosed in FIG. 13, the step of applying a cryogenic treatment may involve applying cooling to at least one autonomic nerve branch. In examples of the method disclosed in FIG. 13, the step of applying a cryogenic treatment involves applying cooling to at least one parasympathetic nerve fiber.

In examples of the method disclosed in FIG. 13, the step of applying a cryogenic treatment may involve applying cooling to at least one sensory nerve fiber.

In examples, for example as disclosed in FIG. 13, a step of applying a cryogenic treatment may involve applying cooling proximate to one or more of the sphenoethmoidal recess, the region proximate to anterior ethmoid nerve, the choanal arch, the region proximate to the posterior ethmoid nerve, and the region along the ethmoid bone proximate to anticipated locations of ethmoid foramina.

In examples, a step of applying a cryogenic treatment to modify a property of the target tissue or tissues nearby the target area may involve altering at least one of a nerve fiber or a blood vessel. In examples, a step of applying a cryogenic treatment to modify a property of the target tissue or tissues nearby the target area may involve modifying the property of a tissue that is at least 3 mm below the mucosal surface. In examples, a step of applying a cryogenic treatment to modify a property of the target tissue or tissues nearby the target area may involve modifying the property of a tissue in such a way that persists for at least 6 months.

Examples of a method, for example as disclosed in FIG. 13, may further include the step of augmenting the application cooling energy by temporarily reducing blood flow through or near the target tissue region. In examples, the step of reducing blood flow through or near the target tissue region involves deploying a pressure application device proximate to the active portion of the treatment instrument. In examples, the step of deploying a pressure application device involves the inflation of a non-compliant balloon that applies a force to tissues proximate to the active portion of the treatment instrument.

An example of a method of applying a hypothermic treatment to a tissue of a patient in order to treat at least one of chronic daily headache, cluster headache, tension headache, migraine, or acute headache symptoms may include the following steps: (1) advancing a therapeutic instrument with an atraumatic distal end configured to deliver cryotherapy into the nostril of the patient; (2) positioning the atraumatic distal end of the instrument against the mucosal wall proximate to at least one posterior nasal nerve or accessory posterior nasal nerve; and (3) applying a cryogenic treatment from the therapeutic instrument to alter mucosal tissue and at least one underlying posterior nasal nerve or accessory posterior nasal nerve in order to treat at least one of chronic daily headache, cluster headache, tension headache, migraine, or acute headache symptoms.

Examples of methods of applying a hypothermic treatment to the sphenopalatine ganglion from within the nasal cavity may include the following steps: (1) advancing a therapeutic instrument configured to deliver cryotherapy into the nostril of the patient; (2) positioning the active portion of the instrument against the mucosal wall proximate to the sphenopalatine foramen; (3) applying a cryogenic treatment from the therapeutic instrument that traverses the mucosal tissue and underlying bone or cartilage tissue and alters at least one property of the sphenopalatine ganglion in order to treat at least one of chronic daily headache, cluster headache, tension headache, migraine, or acute headache symptoms. A diagram of this method is provided in FIG. 14.

In examples of a method, for example as disclosed in FIG. 14, the step of positioning the active portion of the instrument against the mucosal wall proximate to the sphenopalatine foramen may involve positioning the active portion of the instrument in the superior meatus. In examples, a step of positioning the active portion of the instrument against the mucosal wall proximate to the sphenopalatine foramen involves positioning the active portion of the instrument on mucosal tissue overlying the perpendicular plate of the palatine bone. In examples, a step of positioning the active portion of the instrument against the mucosal wall proximate to the sphenopalatine foramen may involve positioning the active portion of the instrument between the middle meatus and the anterior face of the sphenoid sinus. In examples of the method disclosed in FIG. 14, the step of positioning the active portion of the instrument against the mucosal wall proximate to the sphenopalatine foramen is performed in a manner such that no portion of the treatment instrument enters the foramen or otherwise accesses the fossa.

In examples of a method, for example as disclosed in FIG. 14, a step of applying a cryogenic treatment from the therapeutic instrument may be performed such that the cryogen is applied without fracturing or puncturing any bone, cartilage, or mucosal tissue. In examples of a method, for example as disclosed in FIG. 14, a step of applying a cryogenic treatment from the therapeutic instrument may be performed such that the cryogen is applied without fracturing or puncturing any hard tissues, such as cartilage or bone. Quick-healing soft tissues, such as mucosal tissues, may be punctured during the step of applying a cryogenic treatment.

Examples of methods of applying hypothermic treatment into the pterygopalatine fossa may include the following steps: (1) advancing a therapeutic instrument configured to deliver cryotherapy into the nostril of a subject; (2) utilizing a visualization apparatus to guide at least a portion of the therapeutic instrument into the pterygopalatine fossa via the SPF or posterior wall of the maxillary sinus; and (3) applying a cryogenic treatment from the therapeutic instrument to alter at least one property of a target tissue in order to treat at least one of chronic daily headache, cluster headache, tension headache, migraine, or acute headache symptoms.

In examples, step 2 in the previous paragraph may be substituted with a step of confirming the therapeutic instrument is proximate to a target nerve or nerve bundle using a non-visualization technique. This step may be referred to as step 2a.

In examples, step 2a may be included in addition to the original step 2. A diagram of this method is provided in FIG. 15.

In examples, step 2 may be replaced by the alternate workflow described by: utilizing a visualization apparatus to guide at least a portion of the therapeutic instrument into a position such that it can provide a hypothermic treatment into the pterygopalatine fossa.

Figure 15:
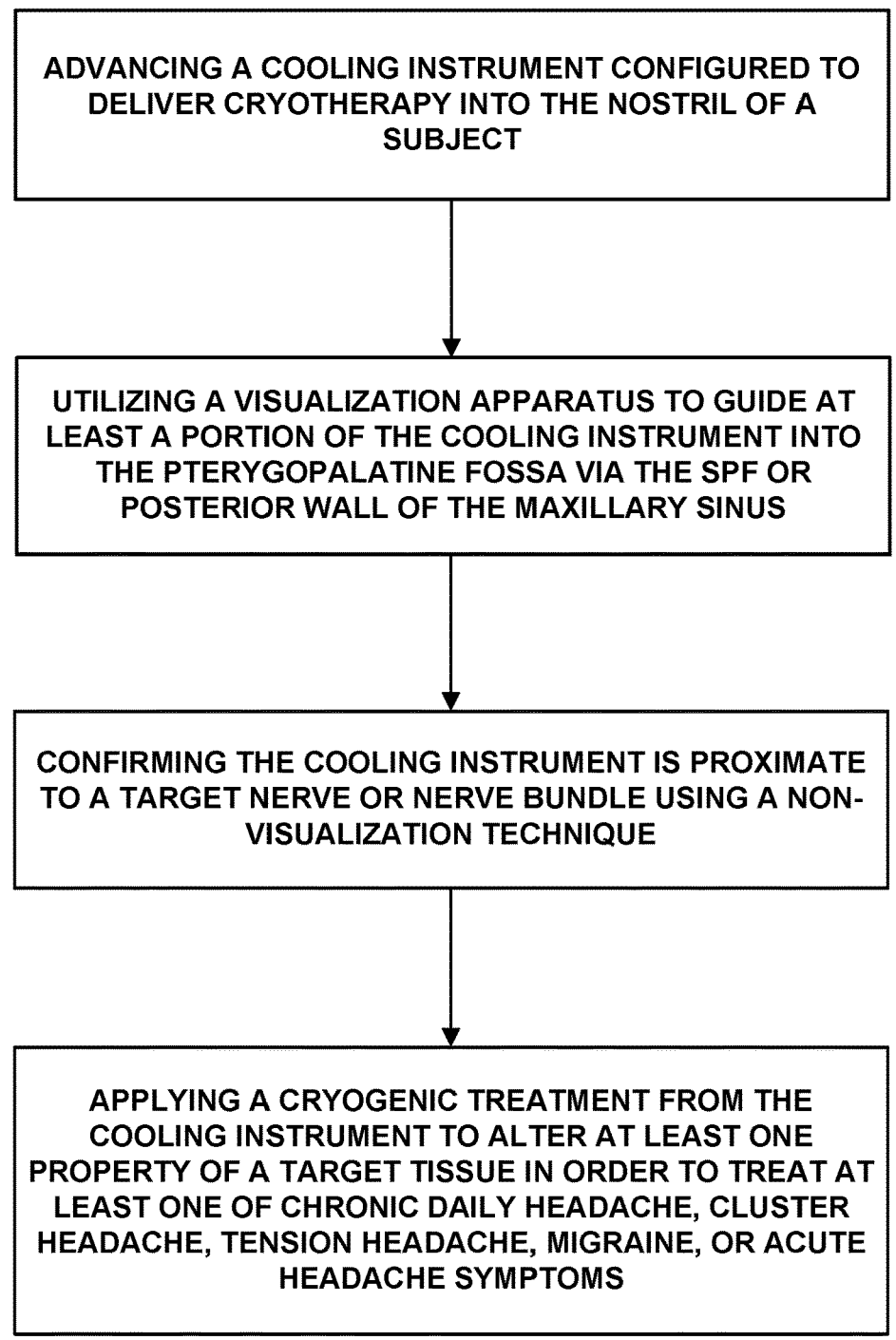
FIG. 15 illustrates another method of use of a therapeutic instrument, according to an example.

Examples of the method disclosed in FIG. 15 further include the step of inserting the visualization apparatus into the nasal cavity. In examples, the visualization apparatus is mounted to a location on the therapeutic instrument. In examples, the visualization apparatus is a separate apparatus that is inserted into the nasal cavity. In examples, the step of utilizing a visualization apparatus involves using an endoscopic camera. In examples, the step of utilizing a visualization apparatus involves using an ultrasound transducer. In examples, the step of utilizing a visualization apparatus involves using one or more infrared radiation sensors.

In examples of a method, for example as disclosed in FIG. 15, a step of utilizing a visualization apparatus to guide the therapeutic instrument may involve inserting the visualization apparatus into the palatine canal via the greater palatine foramen. In examples, the step of utilizing a visualization apparatus to guide the therapeutic instrument involves using a visualization apparatus located external to the body configured to monitor the region proximate to the pterygopalatine fossa. In examples, the step of utilizing a visualization apparatus involves using a fluoroscopic imaging system with or without the injection of a contrast agent.

In examples of a method, for example as disclosed in FIG. 15, a step of confirming the therapeutic instrument is proximate to a target nerve or nerve bundle using a non-visualization technique may involve confirming the instrument is proximate to one of the sphenopalatine ganglion, vidian nerve, or at least one branch of the trigeminal nerve. In examples, a step of confirming the therapeutic instrument is proximate to a target nerve or nerve bundle using a non-visualization technique involves applying an electrical voltage or current to a nerve. Examples may further include a step of assessing the subject for paresthesias as a way to confirm the therapeutic instrument is proximate to a target nerve or nerve bundle.

Examples of methods of applying a hypothermic treatment into the pterygopalatine fossa may include the following steps: (1) advancing a therapeutic instrument configured to deliver cryotherapy into the mouth of a subject; (2)

utilizing a visualization apparatus to guide at least a portion of the therapeutic instrument into the pterygopalatine fossa; (3) confirming the therapeutic instrument is proximate to a target nerve or nerve bundle using a non-visualization technique; and (4) applying a cryogenic treatment from the therapeutic instrument to alter at least one property of a target tissue in order to treat at least one of chronic daily headache, cluster headache, tension headache, migraine, or acute headache symptoms. Examples of methods described in the context of the method disclosed in FIG. 15 may also be applicable to the method described in this paragraph.

Examples of applying a hypothermic treatment to a tissue of a patient in order to eliminate or reduce the degree of trigeminal sensitization may include the following steps: (1) advancing a therapeutic instrument configured to deliver cryotherapy into the nostril of the patient; (2) positioning the instrument proximate to at least one sensory nerve branch of the trigeminal nerve; and (3) applying a cryogenic treatment from the instrument to cool a target tissue and tissues nearby the target area to modify a property of the target tissue or tissues nearby the target area and eliminate or reduce the degree of trigeminal sensitization that occurs due to activation of nerves in or nearby the treated area.

Examples of a method of treating the symptoms of an active headache may include the following steps: (1) introducing a therapeutic instrument stemming from an entirely hand-held system into the anterior portion of the nasal cavity; (2) applying a hypothermic treatment that does not lower tissue temperatures below 5 degrees Celsius into the nasal cavity for no longer than 10 minutes; and (3) removing the therapeutic instrument.

During treatments of certain medical conditions, such as headache, the devices, methods, and systems as disclosed herein may be applied to regions that include or are proximate to the ethmoid sinuses. Treatments may be applied to patients with unaltered ethmoid sinus anatomy, and as such examples may be configured so as to provide cooling to regions with the highly irregular shape and surface area that is associated with the ethmoid sinus region. For example, examples utilize gels, foams, and/or sprays in order to infiltrate cavernous air pockets of the honeycomb-like structure of the ethmoid sinus region without damaging the fragile egg-shell-type bone structures. In other instances, the devices and methods disclosed herein may be used following (immediately following or subsequent to a healing period) ethmoidectomy. Ethmoidectomy is a procedure that involves removing structures that may include the uncinate process, the ethmoid bulla, and others so as to create a widening of the ethmoid sinus. Following this process, it is anticipated that access to certain nerves and blood vessels may be more straightforward and direct. In which case, device examples that utilize direct contact may be preferable for use.

Examples of the inventions described herein may also include delivering therapeutic agents such as antibiotics, anesthetics (including anesthetics used as therapeutic agents), and steroids along with a hypothermic therapy. In examples, the substance may be pre-mixed or integrated into a cryogen and released simultaneously with a hypothermic therapy. In examples, a therapeutic substance can be delivered before or after (or both) a hypothermic therapy is delivered.

Hypothermic therapies may be used both prophylactically to treat chronic headache disorders and as abortive treatments to treat the symptoms of an ongoing headache episode. The inventions described herein may be adapted for use with either treatment paradigm. Further, in addition to hypothermic therapies, in examples other energy modalities may be used both prophylactically to treat chronic headache disorders and as abortive treatments to treat the symptoms of an ongoing headache episode, for example thermal ablation, radiofrequency ablation, and chemical ablation.

Further, the disclosure comprises examples according to the following clauses:

Clause 1. A method for treating or preventing a chronic daily headache, cluster headache, tension headache, migraine, or acute headache of a patient, the method comprising: advancing a non-penetrating cryotherapy element into a nasal cavity of a patient with the cryotherapy element in a first collapsed configuration; contacting the cryotherapy element with a surface of a nasal cavity tissue without penetrating the nasal cavity tissue surface; reconfiguring the cryotherapy element from the first collapsed configuration to a second expanded configuration; and cryogenically cooling a target treatment site with the cryotherapy element in order to treat or prevent a chronic daily headache, cluster headache, tension headache, migraine, or acute headache, wherein the target treatment site comprises at least one nasal nerve tissue or nasal blood vessel.

Clause 2. The method of clause 1, wherein advancing the cryotherapy element into the nasal cavity comprises advancing the cryotherapy element into the inferior meatus.

Clause 3. The method of clause 1, wherein advancing the cryotherapy element into the nasal cavity comprises advancing the cryotherapy element into the superior meatus.

Clause 4. The method of clause 1, wherein advancing the cryotherapy element into the nasal cavity comprises advancing the cryotherapy element into the middle meatus.

Clause 5. The method of any one of clauses 1-4, wherein the nasal blood vessel is a sphenopalatine artery.

Clause 6. The method of any one of claims 1-5, wherein the nasal nerve tissue is a sphenopalatine ganglion, and wherein the sphenopalatine ganglion is cooled through a perpendicular plate of a palatine bone within a superior meatus between a middle turbinate and an anterior face of a sphenoid sinus.

Clause 7. The method of any one of clauses 1-5, wherein the nasal nerve tissue is a posterior nasal nerve or an accessory posterior nasal nerve.

Clause 8. The method of any one of clauses 1-5, wherein the nasal nerve tissue is a nerve branch originating from the sphenopalatine ganglion.

Clause 9. The method of any one of clauses 1-5, wherein the nasal nerve tissue is an autonomic nerve branch.

Clause 10. The method of any one of clauses 1-5, wherein the nasal nerve tissue is a parasympathetic nerve fiber.

Clause 11. The method of clause 10, wherein the parasympathetic nerve fiber is a post-synaptic parasympathetic nerve fibers emerging from a sphenopalatine ganglion.

Clause 12. The method of any one of clauses 1-5, wherein the nasal nerve tissue is a sensory nerve fiber.

Clause 13. The method of any one of clauses 1-12, wherein cryogenically cooling the target treatment site causes damage to mucosal tissue in the nasal cavity.

Clause 14. The method of any one of clauses 1-13, wherein cryogenically cooling the target treatment site causes a reduced blood flow in the nasal blood vessel.

Clause 15. The method of any one of clauses 1-14, further comprising applying pressure to the target treatment site with in order to reduce blood flow in the nasal blood vessel.

Clause 16. The method of any one of clauses 1-15, wherein reconfiguring the cryotherapy element to the second expanded configuration and cryogenically cooling the target treatment site do not cause fracturing or puncturing of nasal bone, cartilage or mucosal tissue.

Clause 17. The method of any one of clauses 1-16, wherein while cryogenically cooling the target treatment site no portion of the cryotherapy element is within the pterygopalatine fossa.

Clause 18. The method of any one of clauses 1-17, wherein the cryotherapy element comprises an expandable structure, and wherein cooling the target treatment site comprises inflating the expandable structure through evaporation of a cryogenic fluid within the expandable structure.

Clause 19. The method of clause 18, wherein cooling the target treatment site comprises cryo-ablating at least one of the nasal blood vessel or nasal nerve tissue.

Clause 20. The method of any one of clauses 18-19, wherein the expandable structure is porous and wherein cooling the target treatment site further comprises evaporation of the cryogenic fluid expelled through pores of the expandable structure.

Clause 21. The method of any one of clauses 18-20, wherein cooling the target treatment site with the cryotherapy element comprises placing a surface of the expandable structure against the target treatment site, and wherein the surface of the expandable structure is configured to provide uniform cooling across the target treatment site.

Clause 22. The method of any one of clauses 18-21, wherein cooling the target treatment site with the cryotherapy element comprises placing a surface of the expandable structure against the target treatment site, and wherein the surface of the expandable structure is configured to provide a substantially uniform cryo-energy distribution along the nasal cavity tissue surface.

Clause 23. The method of clause 22, wherein the expandable structure comprises a first thickness in a middle portion of the surface that is greater than a second thickness at an edge portion of the surface in order to provide uniform cryo-energy distribution along the nasal cavity tissue surface.

Clause 24. The method of any one of clauses 1-23, wherein the cryotherapy element comprises a plurality of tine, wherein the tines, wherein transitioning from the first collapsed configuration to the second expanded configuration causes the tines to fan out, and wherein cooling the target treatment site with the cryotherapy element comprises expelling a cryogenic fluid from the tines onto the target treatment site.

Clause 25. The method of any one of clauses 1-24, wherein advancing the cryotherapy element into the nasal cavity comprises advancing the cryotherapy element into a sphenoethmoidal recess.

Clause 26. The method of any one of clauses 1-24, wherein advancing the cryotherapy element into the nasal cavity comprises advancing the cryotherapy element proximate to a superior turbinate.

Clause 27. The method of any one of clauses 1-24, wherein advancing the cryotherapy element into the nasal cavity comprises advancing the cryotherapy element proximate to an anterior ethmoid nerve.

Clause 28. The method of any one of clauses 1-24, wherein advancing the cryotherapy element into the nasal cavity comprises advancing the cryotherapy element into a maxillary sinus.

Clause 29. The method of any one of clauses 1-24, wherein advancing the cryotherapy element into the nasal cavity comprises advancing the cryotherapy element into a choanal arch.

Clause 30. The method of any one of clauses 1-24, wherein advancing the cryotherapy element into the nasal cavity comprises advancing the cryotherapy element proximate to ethmoid foramina.

Clause 31. The method of any one of clauses 1-30, wherein the nasal nerve tissue is a nerve branch originating from a trigeminal nerve.

Clause 32. The method of any one of clauses 1-31, wherein cryogenically cooling the target treatment site causes cooling of a sphenoethmoidal recess.

Clause 33. The method of any one of clauses 1-32, wherein cryogenically cooling the target treatment site causes cooling of a region proximate to an anterior ethmoid nerve.

Clause 34. The method of any one of clauses 1-33, wherein cryogenically cooling the target treatment site causes cooling of a region proximate to a posterior ethmoid nerve.

Clause 35. The method of any one of clauses 1-34, wherein cryogenically cooling the target treatment site causes cooling of a region along an ethmoid bone proximate to ethmoid foramina.

Clause 36. The method of any one of clauses 1-35, wherein cryogenically cooling the target treatment site causes a reduced degree of trigeminal sensitization.

Clause 37. A method for treating or preventing a chronic daily headache, cluster headache, tension headache, migraine, or acute headache of a patient, the method comprising: advancing a cryotherapy element into a nasal cavity of a patient; advancing at least a portion of the cryotherapy element into a pterygopalatine fossa of the patient; and cryogenically cooling a target treatment site within the pterygopalatine fossa with the cryotherapy element in order to treat or prevent a chronic daily headache, cluster headache, tension headache, migraine, or acute headache, wherein the target treatment site comprises at least one nasal nerve tissue or nasal blood vessel.

Clause 38. The method of clause 37, wherein the nasal blood vessel is a sphenopalatine artery.

Clause 39. The method of clause 37, wherein the nasal nerve tissue is a sphenopalatine ganglion.

Clause 40. The method of clause 37, wherein the nasal nerve tissue is a nerve branch originating from the sphenopalatine ganglion.

Clause 41. The method of clause 37, wherein the nasal nerve tissue is an autonomic nerve branch.

Clause 42. The method of clause 37, wherein the nasal nerve tissue is a parasympathetic nerve fiber.

Clause 43. The method of clause 37, wherein the nasal nerve tissue is a sensory nerve fiber.

Clause 44. The method of any one of clauses 37-43, wherein cryogenically cooling the target treatment site causes a reduced blood flow in the nasal blood vessel.

Clause 45. A method for treating or prevent a chronic daily headache, cluster headache, tension headache, migraine, or acute headache of a patient, the method comprising: advancing a cryotherapy element into a mouth of a patient; advancing at least a portion of the cryotherapy element into a pterygopalatine fossa of the patient; and cryogenically cooling a target treatment site within the pterygopalatine fossa with the cryotherapy element in order to treat or prevent a chronic daily headache, cluster headache, tension headache, migraine, or acute headache, wherein the target treatment site comprises at least one nasal nerve tissue or nasal blood vessel.

Clause 46. The method of clause 45, wherein the nasal blood vessel is a sphenopalatine artery.

Clause 47. The method of any one of clauses 45-46, wherein the nasal nerve is a sphenopalatine ganglion.

Clause 48. The method of any one of clauses 45-47, wherein the nasal nerve is a nerve branch originating from the sphenopalatine ganglion.

Clause 49. The method of any one of clauses 45-46, wherein the nasal nerve is an autonomic nerve branch.

Clause 50. The method of any one of clauses 45-46, wherein the nasal nerve is a parasympathetic nerve fiber.

Clause 51. The method of any one of clauses 45-46, wherein the nasal nerve is a sensory nerve fiber.

Clause 52. The method of any one of clauses 45-51, wherein cryogenically cooling the target treatment site causes a reduced blood flow in the nasal blood vessel.

From the foregoing, it will be appreciated that specific examples of the technology have been described herein for purposes of illustration, but that various modifications can be made without deviating from the spirit and scope of the various examples of the technology. Further, while various advantages associated with certain examples of the technology have been described above in the context of those examples, other examples can also exhibit such advantages, and not all examples need necessarily exhibit such advantages to fall within the scope of the invention. Accordingly, the invention is not limited, except as by the appended claims.

Though the inventions presently-disclosed have primarily been discussed in the context of cryotherapy, the devices, systems, and methods described may have applicability with other ablative and non-ablative surgical techniques. For example, examples may include devices, systems, and methods that utilize heating/hyperthermia therapies. Examples utilizing heating/hyperthermia therapies may be similar in structure, and steps as examples utilizing hypothermic therapies. Sources of heat for use with hyperthermia-based therapies may include RF energy, microwave energy, ultrasound energy, resistive heating, exothermic chemical reactions, combinations thereof and other heat sources known to those skilled in the art. Further, the disclosure may be applied as a standalone system or method, or as part of an integrated medical treatment system. It shall be understood that different aspects of the disclosure can be appreciated individually, collectively, or in combination with each other.

The methods described herein can be utilized effectively with any of the examples or variations of the devices and systems described above, as well as with other examples and variations not described explicitly in this document. The features of any of the systems or system components described in any of the examples herein can be used in any other suitable example of a system or system component.

By the term "about," "approximately," or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It should be understood from the foregoing that, while particular implementations have been illustrated and described, various modifications can be made thereto and are contemplated herein. It is also not intended that the disclosure be limited by the specific examples provided within the specification. Furthermore, it shall be understood that all aspects of the disclosure are not limited to the specific depictions, configurations, or relative proportions set forth herein which depend upon a variety of conditions and variables. Various modifications in form and detail of the examples of the disclosure will be apparent to a person skilled in the art. It is therefore contemplated that the disclosure shall also cover any such modifications, variations, and equivalents.

We claim:

1. A method for treating or preventing a chronic daily headache, a cluster headache, a tension headache, a migraine, or an acute headache of a patient, the method comprising:

advancing a non-penetrating cryotherapy element into a nasal cavity of a patient with the cryotherapy element in a first collapsed configuration;

contacting the cryotherapy element with a surface of a nasal cavity tissue without penetrating the surface of the nasal cavity tissue;

reconfiguring the cryotherapy element from the first collapsed configuration to a second expanded configuration; and cryogenically cooling a target treatment site with the cryotherapy element in order to treat or prevent a chronic daily headache, a cluster headache, a tension headache, a migraine, or an acute headache, wherein the target treatment site comprises a nerve branch originating from a trigeminal nerve.

2. The method of claim 1, wherein advancing the cryotherapy element into the nasal cavity comprises advancing the cryotherapy element into one of (i) the inferior meatus, (ii) the superior meatus, or (iii) the middle meatus.

3. The method of claim 1, wherein the target treatment site further comprises a nasal blood vessel, and wherein the nasal blood vessel is a sphenopalatine artery.

4. The method of claim 1, wherein cryogenically cooling the target treatment site causes damage to mucosal tissue in the nasal cavity and/or causes a reduced blood flow in the nasal blood vessel.

5. The method of claim 1, further comprising applying pressure to the target treatment site with in order to reduce blood flow in the nasal blood vessel.

6. The method of claim 1, wherein reconfiguring the cryotherapy element to the second expanded configuration and cryogenically cooling the target treatment site do not cause fracturing or puncturing of nasal bone, cartilage or mucosal tissue.

7. The method of claim 1, wherein while cryogenically cooling the target treatment site no portion of the cryotherapy element is within a pterygopalatine fossa.

8. The method of claim 1, wherein the cryotherapy element comprises an expandable structure, and wherein cooling the target treatment site comprises one or more of (i) inflating the expandable structure through evaporation of a cryogenic fluid within the expandable structure, (ii) cryo-ablating at least one of the nasal blood vessel or nasal nerve tissue, (iii) evaporation of the cryogenic fluid expelled through pores of the expandable structure, (iv) placing a surface of the expandable structure against the target treatment site, and wherein the surface of the expandable structure is configured to provide uniform cooling across the target treatment site, or (v) placing a surface of the expandable structure against the target treatment site, and wherein the surface of the expandable structure is configured to provide a substantially uniform cryo-energy distribution along the surface of the nasal cavity tissue.

9. The method of claim 1, wherein the cryotherapy element comprises an expandable structure positioned on an insulating material, wherein the insulating material comprises a first thickness in a middle portion of the insulating material that is greater than a second thickness at an edge portion of the insulating material.

10. The method of claim 1, wherein the cryotherapy element comprises a plurality of tines, wherein the plurality of tines, when transitioning from the first collapsed configuration to the second expanded configuration, causes the plurality of tines to fan out, and wherein cooling the target treatment site with the cryotherapy element comprises expelling a cryogenic fluid from the tines onto the target treatment site.

11. The method of claim 1, wherein advancing the cryotherapy element into the nasal cavity comprises one of (i) advancing the cryotherapy element into a sphenoethmoidal recess, (ii) advancing the cryotherapy element proximate to a superior turbinate, (iii) advancing the cryotherapy element proximate to an anterior ethmoid nerve, (iv) advancing the cryotherapy element into a maxillary sinus, (v) advancing the cryotherapy element into a choanal arch, or (vi) advancing the cryotherapy element proximate to ethmoid foramina.

12. The method of claim 1, wherein cryogenically cooling the target treatment site causes one or more of (i) cooling of a sphenoethmoidal recess, (ii) cooling of a region proximate to an anterior ethmoid nerve, (iii) cooling of a region proximate to a posterior ethmoid nerve, (iv) cooling of a region along an ethmoid bone proximate to ethmoid foramina, or (v) a reduced degree of trigeminal sensitization.

\* \* \* \* \*